United States Patent [19]
Sharpe et al.

[11] Patent Number: 5,637,314
[45] Date of Patent: *Jun. 10, 1997

[54] TOPICAL AND SYSTEMIC APPLICATION OF BUSPIRONE OR DERIVATIVES THEREOF FOR TREATING ATOPIC DERMATITIS

[75] Inventors: Richard J. Sharpe, Gloucester; Kenneth A. Arndt, Newton Centre; Stephen J. Galli, Winchester, all of Mass.

[73] Assignee: Beth Israel Deaconess Medical Center, Inc., Boston, Mass.

[*] Notice: The term of this patent shall not extend beyond the expiration date of Pat. No. 5,484,788.

[21] Appl. No.: 477,767

[22] Filed: Jun. 7, 1995

[51] Int. Cl.$^6$ .............................. A61F 2/02; A61F 9/02; A61L 15/16; A61K 31/505
[52] U.S. Cl. .............. 424/445; 424/423; 424/427; 424/430; 424/434; 424/435; 424/436; 424/437; 424/451; 424/464; 514/275
[58] Field of Search .............. 514/275; 424/423, 424/427, 430, 434, 435, 436, 437, 445, 451, 464

[56] References Cited

U.S. PATENT DOCUMENTS

| | | | |
|---|---|---|---|
| 3,717,634 | 2/1973 | Wu et al. | 260/256.4 N |
| 3,976,776 | 8/1976 | Wu et al. | 424/251 |
| 4,182,763 | 1/1980 | Casten et al. | 424/251 |
| 4,351,939 | 9/1982 | Simms et al. | 544/230 |
| 4,417,049 | 11/1983 | Sims | 544/231 |
| 4,438,119 | 3/1984 | Allen et al. | 424/251 |
| 4,468,391 | 8/1984 | Voith | 424/244 |
| 4,515,947 | 5/1985 | Sandefur et al. | 544/295 |
| 4,620,006 | 10/1986 | Sandefur et al. | 544/402 |
| 4,634,703 | 1/1987 | Kurtz et al. | 514/252 |
| 4,636,563 | 1/1987 | Abou-Gharbia | 546/87 |
| 4,640,921 | 2/1987 | Othmer et al. | 514/252 |

(List continued on next page.)

FOREIGN PATENT DOCUMENTS

| | | |
|---|---|---|
| 170213 | 7/1985 | European Pat. Off. |
| 223344 | 9/1986 | European Pat. Off. |
| 440851 | 2/1990 | European Pat. Off. |
| 442423 | 2/1991 | European Pat. Off. |
| 497314 | 8/1992 | European Pat. Off. |
| 2654934 | 5/1991 | France. |
| 2089341 | 6/1982 | United Kingdom. |
| 2139217 | 11/1984 | United Kingdom. |
| WO88/07529 | 10/1988 | WIPO. |
| WO92/00070 | 1/1989 | WIPO. |
| WO89/03676 | 5/1989 | WIPO. |
| WO89/4311 | 5/1989 | WIPO. |
| WO91/02497 | 3/1991 | WIPO. |

(List continued on next page.)

OTHER PUBLICATIONS

Allen, L.E., et al., "Pharmacologic Effects of MJ 9022-1, a Potential tranquilizing Agent," *Arneimittel-Forsch*, 24:917 (1974)*.

Ameisen, J.C., et al., "A New Interpretation of the Involvement of Serotonin in Delayed-Type Hypersensitivity," *J. Immunology*, 142:(9):3171-3179 (1989)*.

Arndt, K.A., et al., "The Pharmocology of Topical Therapy," *Dermatology in General Medicine*, Ch. 211, 2532-40, T.B. Fitzpatrick, A.Z. Eisen, K. Wolff, I.M., Freedberg and K.F. Austen, eds., 3d ed., McGraw Hill, Inc., New YOrk (1987)*.

Backerman, "Premenstrual syndrome Update—1991," *Md. Med. J.* 40:1003-1009 (1991).

Balster, et al., "IntravenousBuspirone Self-Administration in Rhesus Monkeys," *J. Clin. Psychiatry*, 43:34-39 (1982).

(List continued on next page.)

*Primary Examiner*—Carlos Azpuru
*Attorney, Agent, or Firm*—Kilpatrick Stockton LLP

[57] ABSTRACT

A method for treating atopic dermatitis, hayfever, asthma and pruritis that includes topical or systemic application of an effective amount of buspirone or a buspirone derivative or its pharmaceutically acceptable salt, other than a quaternary salt, optionally in a pharmaceutically-acceptable diluent or carrier.

32 Claims, 12 Drawing Sheets

U.S. PATENT DOCUMENTS

| | | | |
|---|---|---|---|
| 4,687,772 | 8/1987 | Alderdice | 514/273 |
| 4,696,927 | 9/1987 | Gittos et al. | 514/236 |
| 4,709,027 | 11/1987 | Abou-Gharbia et al. | 544/6 |
| 4,732,984 | 3/1988 | Abou-Gharbia et al. | 544/295 |
| 4,748,240 | 5/1988 | Stack et al. | 544/47 |
| 4,777,173 | 10/1988 | Shrotryia et al. | 514/252 |
| 4,788,189 | 11/1988 | Glazer | 514/221 |
| 4,810,789 | 3/1989 | Behme et al. | 544/230 |
| 4,812,567 | 3/1989 | Abou-Gharbia | 544/230 |
| 4,851,533 | 7/1989 | Abou-Gharbia | 544/405 |
| 4,883,875 | 11/1989 | Abou-Gharbia | 546/16 |
| 4,895,848 | 1/1990 | Traber et al. | 514/255 |
| 4,900,835 | 2/1990 | Abou-Gharbia | 546/272 |
| 4,927,934 | 5/1990 | Abou-Gharbia et al. | 546/152 |
| 4,940,585 | 7/1990 | Hapworth et al. | 424/464 |
| 4,943,428 | 7/1990 | Lucot et al. | 424/10 |
| 4,963,557 | 10/1990 | Badger et al. | 514/278 |
| 5,015,646 | 5/1991 | Simms | 514/253 |
| 5,032,578 | 7/1991 | Horovitz | 514/19 |
| 5,053,508 | 10/1991 | Schiehser et al. | 544/357 |
| 5,096,908 | 3/1992 | Gidda et al. | 514/307 |
| 5,098,889 | 3/1992 | Costall et al. | 514/19 |
| 5,114,947 | 5/1992 | Imondi | 514/282 |
| 5,134,140 | 7/1992 | Stack | 514/212 |
| 5,162,322 | 11/1992 | Taylor, Jr. et al. | 514/252 |
| 5,167,616 | 12/1992 | Haak et al. | 604/20 |
| 5,169,638 | 12/1992 | Dennis et al. | 424/457 |
| 5,183,819 | 2/1993 | Abou-Gharbia et al. | 514/255 |
| 5,185,329 | 2/1993 | Gawin et al. | 514/159 |
| 5,187,277 | 2/1993 | Komissarov et al. | 544/362 |
| 5,244,902 | 9/1993 | Sharpe et al. | 514/278 |
| 5,256,408 | 10/1993 | Babcock et al. | 424/78.04 |
| 5,290,783 | 3/1994 | Sharpe et al. | 514/278 |
| 5,484,788 | 1/1996 | Sharpe et al. | 514/275 |

FOREIGN PATENT DOCUMENTS

| | | |
|---|---|---|
| WO91/02527 | 3/1991 | WIPO. |
| WO91/13622 | 9/1991 | WIPO. |
| WO92/09252 | 6/1992 | WIPO. |
| WO92/19226 | 11/1992 | WIPO. |
| WO93/04681 | 3/1993 | WIPO. |
| WO93/12789 | 7/1993 | WIPO. |
| WO94/22448 | 10/1994 | WIPO. |

OTHER PUBLICATIONS

Barbee, et al., "A Comparison of the Single–Dose Effects of Alprazolam, Buspirone, and Placebo Upon Memory Function," *J. Clin. Psychopharmacol.*, 11:351–356 (1991).

Blozovski and Sivadjian, "The Action of Serotonin, Reserpine and Other Pharmacological Agents on Sudoral Secretion", *Chemical Abstracts*, 54:21504 (1960)*.

Bohn and Gammans, "Buspirone Therapy for Elderly Patients with Anxiety or Depressive Neurosis," *J. Clin. Psychiatry*, 51:309 (1990).

Bowden, et al., "New Developments in the Treatment of Anxiety Disorders," *Texas Medicine*, 84:38–42 (1988).

Bruning, et al., "Quantitative Autoradiographic Distribution and Pharmacological Characterization of (3H) Buspirone Binding to Sections from Rat, Bovine and Marmoset Brain," *J. Neural Transm*, 78:131–144 (1989).

Bruno, "Buspirone in the Treatment of Alcoholic Patients," *Psychopathology*, 1:49–59 (1989).

Budhram, et al., "Some Putative Non–Sedating Anxiolytics in a Bonditioned Licking Conflict," *Brit. J. Pharmacol.*, 88:331P (1986).

Caccia, S., et al., "Disposition and Metabolism of Buspirone and its Metabolite 1–(2–Pyrimidinyl)–piperazine in the Rat," *Xenobiotica*, 13(3):147–153 (1983)*.

Caccia, et al., "Identification and Quantitation of 1–(2–pyrimidinyl)piperazine, an Active Metabolite of the Anxiolytic Agent Buspirone, in Rat Plasma and Brain," *J. Chromatogr.*, 252:310–314 (1982).

Caccia, et al., "Disposition of the Psychotropic Drugs Buspirone, MJ–13805 and Piribedil, and of Their Common Active Metabolite 1–(2–Pyrimindinyl)–Piperazine in the Rat," *Xenobiotica*, 15:835–844 (1985).

Caccia, et al., "1–(2–Pyrimidinyl)–Piperazine as Active Metabolite of Buspirone in Man and Rat," *Pharmacology*, 33:46–51 (1986).

Carli, et al., "Effect of 5–HT$_{1A}$Agonists on Stress–Induced Deficit in Open Field Locomotor Activity of Rats: Evidence That This Model Identifies Anxiolytic–Like Activity," *Neuropharacology*, 285:471–476 (1989).

Cimino, et al., "Dopaminergic Effects of Buspirone, a Novel Anxiolytic Agent," *Biochem. Pharmacol.*, 32:1069–1074 (1983).

Coffman, J.D., "The Attenuation by Reserpine or Guanethidine of the Cutaneous Vasoconstriction caused by Tobacco smoking," *Amer. Heart J.*, vol. 74, No. 2, pp. 229–234 (1967).

Cohn, et al., "Low–Sedation Potential of Buspirone Compared with Alprazolam and Lorazepam in the Treatment of Anxious Patients: a Double–Blind Study," *J. Clin. Psychiatry*, 47:409–412 (1986).

Dommisee, et al., "Formulating Forum Buspirone: a New Type of Anxiolytic," *Drug Intell. Clin. Pharm.*, 19:624–627 (1985).

Dostal, G. and Gamelli, R.L., "The Differential Effect of Corticosteroids on Wound Disruption Strength in Mice," *Arch. Surg.*, vol. 125, pp. 636–640 (1990)*.

Eison, A.S., Temple, D.L. "Buspirone: Review of its Pharmacology and Current Perspectives on its Mechanism of Action," *Am. J. Med.*, 80(Supp. 3B):1–9 (1986)*.

Feighner, "Buspirone in the Long–Term Treatment of Generalized Anxiety Disorder," *J. Clin. Psychiatry*, 48:3–6 (1987).

Fishel, R., et al., "Cyclosporin A Impairs Wound Healing In Rats," *J. Surg. Research*, 34:572–575 (1983)*.

Freire–Garabal, et al., "Effects of Buspirone on the Immunosuppressive Response to Stress in Mice," *Arch. Int. Pharmacodyn Ther.*, 314:160–168 (1991)*.

Galli and Hammel, "Unequivocal Delayed Hypersensitivity in Mast Cell–Deficient and BeigeMice", *Science*, 226:710–13 (1984)*.

Gammans, et al., "Buspirone Disposition in Rhesus Monkeys," *Fed. Proc., Drug Disposition*, 2316:634 (1981).

Gammans, et al., "Concentration of Buspirone and 1–Pyrimidinylpiperazine, a Metabolite, in Rat Brain," *Fed. Proc., Metabolism and Disposition: Absorption, Distribution, and Excretion*, 495:377 (1983).

Gammans, "The Effects of Buspirone Binding of Digoxin, Dilantin, Propanolol and Warfarin to Human Plasma," *Fed. Proc., Drug Binding*, 4165:1123 (1985).

Gammans, et al., "Metabolism and Disposition of Buspirone," *Am. J. Med.*, 80 (Supp. B):41–51 (1986).

Gammans, et al., "Pharmacokinetics of Buspirone in Elderly Subjects," *J. Clin. Pharmacol.*, 29:72–78 (1989).

Garrattini, et al., "Notes on Buspirone's Mechanisms of Action," *J. Clin. Psychiatry*, 43:19–24 (1982).

Geller and Hartmann, "Effects of Buspirone on Operant Behavior of Laboratory Rats and Cynomolgus Monkeys," *J. Clin. Psychiatry*, 43:25–33 (1982).

Glaser and Traber, "Buspirone Action on Serotinin Receptors in Calf Hippocampus," *Eur. J. Pharmacol.*, 88:137–138 (1983).

Goa, K.L. and Ward, A., "Buspirone: A Preliminary Review of its Pharmacological Properties and Therapeutic Efficacy as an Anxiolytic," *Drugs*, vol. 32, pp. 114–129 (1986)*.

Goldberg, "Buspirone Hydrochloride: a Unique new Anxiolytic Agent. Pharmacokinetics, Clinical Pharmacology, Abuse Potential and Clinical Efficacy," *Pharmacotherapy*, 4:315–324 (1984).

Goldberg, L., and Finnerty, R., "Comparative Efficacy of Buspirone and Diazepam in the Treatment of Anxiety," *Am. J. Psychiatry*, vol. 136, No. 9, pp. 1184–1187 (1979)*.

Gozlan, et al., "Identification of Presynaptic Serotinin Autoreceptors Using a New Ligand: $^3$H–PAT," *Nature* (London), Griffith, et al., "Investigation of the Abuse Liability of Buspirone in Alcohol–Dependent Patients," *Am. J. Med.*, 80:30–35 (1986).

Hanifin, "Atopic Dermatitis: New Therapeutic Considerations," *J. Am. Acad. Dermatol.*, 24:1097–1101 (1991).

Hart, et al., "Effects of Buspirone and Alprazolam on the Cognitive Performance of Normal Elderly Subjects," *Am. J. Psychiatry*, 148:73–77 (1991).

Hendry and Balster., "Discriminative Stimulus Properties of Buspirone Compared to Central Nervous System Depressants in Rats," *Pharmacol, Biochem. Behav.*, 19:97–101 (1983).

Hellstrand, K., and Hermodsson,m S., "Role of Serotonin in the Cell Regulation of Human Natural Killer Cell Cytotoxicity," *J. Immunology*, 139(3):pp. 869–875 (1987)*.

Jacobson, et al., "Comparison of Buspirone and Diazepam in Generalized Anxiety Disorder," *Pharmacotherapy*, 5(5):290–296 (1985).

Jajoo, et al., "Metabolism of the Antianxiety Drug Buspirone in the Rat," *Drug Metab. Dispos. Biol. Fate Chem.*, 17:625–633 (1989).

Jajoo, et al., "In Vitro Metabolism of the Antianxiety Drug Buspirone as a Predictor of its Metabolism in Vivo," *Xenobiotica*, 20:779–786 (1990).

Jann, M.W., "Buspirone: An Update on a Unique Anziolytic Agent," *Pharmacotherapy*, 8(1):100–116 (1988)*.

Jenike, "Buspirone Augmentation of Fluoxetine in Patients with Obsessive Compulsive Disorder," *J. Clin. Psychiatry*, 52:13–14 (1991).

Judd, et al., "Buspirone and Fluoxetine in the Treatment of OCD," *Aust. N Z J. Psychiatry*, 26:684–686 (1992).

Jun, D.D., et al., "Parallel Recovery of Epidermal Antigen–Presenting Cell Activity and Contact Hypersensitivity Responses in MIce Exposed to Ultraviolet Irradiation: The Role of a Prostaglandin–Dependent Mechanism," *J. Invest. Dermatol.*, 90:311 (1988).

Kadota, et al., "Acute Toxicity Study of Buspirone Hydrochloride in Mice, Rats and Dogs," *J. Toxicol. Sci.*, 1:1–14 (199).

Kai, et al., "Reproductive and Developmental Toxicity Studies of Buspirone Hydrochloride (I)–Oral Administration to Rats During the Period of Fetal Organogenesis," *J. Toxicol. Sci.*, 1:31–60 (1990).

Kai, et al., "Reproductive and Developmental Toxicity Studies of Buspirone Hydrochloride (II)–Oral Administration to Rats During Perinatal and Lactation Periods," *J. Toxicol. Sci.*, 1:61–84 (1990).

Kaulen, et al., "Autoradiographic Localization of [3H]Buspirone Binding Sites in Rat Brain," *Neurosci. Lett.*, 53:191–195 (1985).

Kawano et al., "Antigenicity Study of Buspirone Hydrochloride in Guinea Pigs and Mice," *J. Toxicol. Sci.*, 1:15–30 (1990).

Knapp, "Clinical Profile of Buspirone," *Br. J. Clin. Pract. Symp. Suppl. (AVL)*, 38:95–99 (1985).

Kligman, "The Comparative Histopathology of Male–Pattern Baldness and Senescent Baldness," *Clinics in Dermatology*, 6(4):108–118 (1988)*.

Kolosa, et al., "Neurochemical Effects of Buspirone, a Novel Psychotropic Drug, on the Central Cholinergic System," *J. Pharm. Pharmacology*, 34:317–317 (1982).

Kranzler, "Use of Buspirone in an Adolescent with Overanxious Disorder," *J. Am. Acad. Child, Adolesc. Psychiatry*, 27:789–790 (1988).

Lader, "Discussant Presentation," *J. Clin. Psychiatry*, 43:12(Sec. 2):80 (1982).

Lader, "Clinical Pharmacology of Non–Benzodiazepine Anxiolytics," *Pharmacol. Biochem. Behav.*, 29:797–798 (1988).

Lawlor, et al., "A Single Oral Dose Challenge of Buspirone Does Not Affect Memory Processes in Older Volunteers," *Biol. Psychiatry*, 32:101–103 (1992).

Lebert, et al., "Euphoria with Buspirone After Fluoxetine Treatment," *Am. J. Psychiatry*, 150:167 (1993).

Leonard, "Neuropharmacological Profile of Buspirone, a Non–Benzodiazepine Anxiolytic with Specific Mid–Brain Modulating Properties," *Br. J. Clin. Pract. Symp. Suppl.*, 38:74–82 (1985).

Malcolm, et al., "A Placebo–Controlled Trial of Buspirone in Anxious Impatient Alcoholics," *Alcohol Clin. Exp. Res.*, 16:1007–1013 (1992).

Markovitz, et al., "Buspirone Augmentation of Fluoxetine in Obsessive–Compulsive Disorder," *Am. J. Psychiatry*, 147:798–800 (1990).

Matheson, et al., "A Comparioson of the Effects of Buspirone and Diazepam on Plasma Cortisosterone Levels in Rat," *Neuropharmacology*, 27:823–830 (1988).

McMillen and Mattiace, "Comparative Neuropharmacology of Buspirone and MJ–13805, a Potential Anti–Anxiety Drug", *J. Neural Transm.*, 57:255–265 (1983).

Medawar, "Data Sheets: a Consumer Perspective," *Lancet*, 1:777–778 (1988).

Meltzer and Fleming, "Effect of Buspirone on Prolactin and Growth Hormone Secretion in Laboratory Rodents and Man," *J. Clin. Psychiatry*, 43:76–79 (1982).

Metz, "Interaction Between Fluoxetine and Buspirone," *Can. J. Psychiatry*, 35:722–723 (1990).

Metys, J., et al., "Inhibition of Passive cutaneous Anaphalaxis By Several Histamine ($H_1$) and Serotonin Antagonists in the Rat," *Agents and Actions*, 23:331–333 (1988).

Milburn, C.M., and Peroutka, S.J., "Characterization of [$^3$H]Quipazine Binding to 5-Hydroxytryptamine$_3$ Receptors in Rat Brain Membranes," *J. Neurochem.*, 52:1787–1792 (1989)*.

Molitor, "Effect of Buspirone on Mixed function Oxidase in Rats," *Fed. Proc., Drug Metabolism and Biotransformation*, 4950:1257 (1985).

Moon and Taylor, "in Vitro Autoradiography of 3H–Buspirone and 3H–2–Deoxyglyglucose After Buspirone Administration," *Soc. Neurosci. Abst.*, 348:114 (1985).

Moskowitz and Smiley, "Effects of Chronically Administered Buspirone and Diazepam on Driving–Related Skills Performance," *J. Clin. Psychiatry*, 43:45–55 (1982).

Murasaki, et al., "Phase I Study of a New Antianxiety Drug, Buspirone," *Prog. Neuropsychopharmacol. Biol. Psychiatry*, 13:137–144 (1989).

Napoliello and Domantay, "Buspirone: a Worldwide Update," *Br. J. Psychiatry Suppl.*, 12:40–44 (1991).

New, J.S., et al., "Buspirone Analogues, 2. Structure–Activity Relationships of Aromatic Imide Derivatives," *J. Med. Chem.*, vol. 29, pp. 1476–1482 (1986).

Package Insert—Buspar™.

Physician's Desk Reference; 48th Edition (1994).

Popper, "Psychopharmacologic Treatment of Anxiety Disorders in Adolescents and Children" *J. Clin. Psychiatry*, 54:52–63 (1993).

Rakel, "Long–term Buspirone Therapy for Chronic Anxiety: a Multicenter International Study to Determine Safety," *South Med. J.*, 83:194–198 (1990).

Riblet, et al., "Pharmacology and Neurochemistry of Buspirone," *J. Clin. Psychiatry*, 43:11–18 (1982).

Rickels, et al., "Long–term Treatment of Anxiety and Risk of Withdrawal. Prospective Comparison of Clorazepate and Buspirone," *Arch. Gen. Psychiatry*, 45;444–450 (1988).

Rickels, et al., "Buspirone in Treatment of Premenstrual Syndrome," *Lancet*, 1:777 (1989).

Rickels and Schweizer, "The Clinical Course and Long–Term Management of Generalized Anxiety Disorder," *J. Clin. Psychopharmacol.*, 10:101S–110S (1990).

Sanghera, et al., "Buspirone a Non–Benzodiazepine Anxiolytic, Increase Locus Coerleus Noradrenergic Neuronal Activity," *Europ. J. Pharmacol.*, 86:107–110 (1983).

Sathananthan et al., "Correlation Between Neuroleptic Potential and Stereotypy," *Curr. Therp. Res.*, 18:701–705 (1975).

Schroeder and Christophers, "Transient Absence of C5a–Specific Neutrophil Function in Inflammatory Disorders of the Skin", *The Journal of Investigative Dermatology*, 85:194–98 (1985)*.

Schweizer, et al., "Open Trial of Buspirone in the Treatment of Major Depressive Disoreder," *Psychopharmacol. Bull.*, 22:183–185 (1986).

Sellers, et al., "Comparative Drug Effects and Abuse Liability of Lorazepam, Buspirone, and Secobarbital in Nondependent Subjects," *J. Clin. Psychopharmacol.*, 12:79–85 (1992).

Simeon, et al., "Pharmacotherapy of Childhood Anxiety Disorders," *Clin. Neuropharmacol.*, 15:229A–230A (1992).

Seppala, T., et al., "Effects of Alcohol on Buspirone and Lorazepam Actions," *Clin. Pharmacol. Ther.*, 201–207 (1982)*.

Singh, G., "Cortiocsteroids in Corneal Endothelial Wound Healing," *Annals of Opthalmology*, 17:(1):pp. 238–245 (1985)*.

Skolnick, et al., "Preclinical Pharmacology of Buspirone Hydrochloride," *Pharmacotherapy*, 4:308–314 (1984).

Spector, "Drug Therapy Review," *Iowa Medicine*, 292–295 (1987).

Sternlicht, et al., "Obsessive–compulsive Disorder, Fluoxetine, and Buspirone," *Am. J. Psychiatry*, 150:526 (1993).

Sussman, "Treating Anxiety While Minimizing Abuse and Dependence," *J. Clin. Psychiatry*, 54:44–51 (1993).

Taylor, et al., "Changing Concepts of the Biochemical Action of the Anxioselective Drug Buspirone," *Drug. Dev. Res.*, 4:95–108 (1984).

Taylor, D.P., "Buspirone, a New Approach to the Treatment of Anxiety," *Faseb J.*, vol. 2, pp. 2445–2452 (1988)*.

Taylor, et al., "Pharmacological and Clinical Effects of Buspirone," *Pharmacol. Biochem. Behav.*, 23:687–694 (1985).

Tiller, et al., "Short–Term Buspirone Treatment in Disinhibition with Dementia," *Lancet*, 2:510 (1988).

Tiller, "The New and Newer Antianxiety Agents," *Med. J. Aust.*, 151:697–701 (1989).

Tompkins, et al., "Inhibition of Aggressive Behavior in Rhesus Monkeys by Buspirone," *Research Communications in Psychology, Psychiatry and Behavior*, 5:337–352 (1980).

Tucker, "Inflammation in Acne Vulgaris: Leukocyte Attraction and Cytotoxicity by Comedonal Material", *The Journal of Investigative Dermatology*, 74:21–25 (1980)*.

Tunnicliff, "Molecular Basis of Buspirone Anxiolytic Action," *Pharm. Toxicol.*, 69:149–156 (1991).

vanWauwe, P., and Goossens, J.G., "Arabinogalactan– and Dextran–induced Ear Inflammation in Mice: Differential Inhibition by H1–antihistamines, 5–HT–Serotonin Anatagonists and Lipoxygenase Blockers," *Agents and Actions*, 28:78–82 (1989)*.

Vogel, et al., "A Simple and Reliable Conflict Procedure for Testing Anti–Anxiety Agents," *Psychopharmacology* (Berlin), 21:1–7 (1971).

Wershil et al., "Mast Cell–Dependent Amplification of an Immunologically Nonspecific Inflammatory Response", *Journal of Immunology*, 140:2356–60 (1988)*.

Witkin, et al., "Behavorial Studies with Anxiolytic Drugs. IV. Serotonergic Involvement in the Effects of Buspirone on Punished Behavior of Pigeons," *J. Pharmacol. Exp. Ther.*, 243:970–977 (1987).

Wong, D.T.W., et al., "Human Eosinophils Express Transforming Growth Factor–Alpha," *J. Exp. Chem.*, 172:673–681 (1990)*.

Wong, D.T.W., et al., "Eosinphils From Patients with Blood Eosinophilia Express Transforming Growth Factor $\beta 1$," *Blood*, 78:2702–2707 (1991)*.

Yudofsky, Wu, et al., "Pharmacologic Management of Arggresion in the Elderly," *J. Clin. Psychiatry*, 51:22–32 (1990).

"Buspirone—an Alternative Drug for Anxiety?" *Drug Ther. Bull.*, 27:27–28 (1989).

"Buspirone Hydrochloride Tablets In vivo Bioequivalence and In Vitro Dissolution Testing", *FDA Guidance Document*, (1993).

Freire–Garabal, M., et al, "Effects of Buspirone on the Immunosuppresive Response to Stress in Mice", Arch. Int. Pharmacodyn, 314, 160–168 (1991).

TOPICAL AND SYSTEMIC APPLICATION OF BUSPIRONE OR DERIVATIVES THEREOF FOR TREATING ATOPIC DERMATITIS

FIELD OF THE INVENTION

This invention is in the area of the treatment of atopic dermatitis using buspirone or its pharmaceutically acceptable salt or derivative. This application claims priority to Ser. No. 08/037,225, filed Mar. 26, 1993, now allowed and Ser. No. 08/037,271, filed on Mar.26, 1993, now U.S. Pat. No. 5,484,788.

BACKGROUND OF THE INVENTION

Atopic dermatitis is a chronic inflammatory skin disorder exhibited by individuals with a hereditary predisposition to a lowered cutaneous threshold to pruritis, often accompanied by allergic rhinitis, hay fever, and asthma, and primarily characterized by extreme itching, leading to scratching and rubbing that in turn results in the typical lesions of eczema. In infants (infantile eczema), there is a predilection for occurrence of the cheeks, which may extend to other areas of the body; in children, adolescents and adults, it is found chiefly on the flexural surfaces (flexural eczema), especially on the antecubital and popiteal areas, and on the neck, eyelids, and wrists and behind the ears.

In atopic dermatitis, and eczema in general, immunologically mediated leukocyte infiltration (particularly infiltration of mononuclear cells, lymphocytes, neutrophils, and eosinophils) into the skin significantly contributes to the pathogenesis of these diseases. Chronic eczema also is associated with significant hyperproliferation of the epidermis.

Atopic dermatitis and eczema, if sufficiently severe, can lead to death. Less serious, but uncomfortable and often painful symptoms associated with atopic dermatitis include itching, swelling, redness, blisters, crusting, ulceration, pain, scaling, cracking, hair loss, scarring, or oozing of fluid involving the skin, eye, or mucosal membranes.

The need to control atopic dermatitis has led to a search for therapeutic agents that are both safe and effective. Corticosteroids, when administered systemically, are effective in this regard but are associated with significant and potentially dangerous side effects. Topically applied corticosteroids have some efficacy in treating these conditions, but are only partially effective in many instances and have their own significant side effects, including atrophy of tissue, formation of telangiectasia, blanching, and a myriad of systemic effects if significantly absorbed. Other agents with partial utility for treating some of the above conditions include psoralen plus ultraviolet A (PUVA), cyclosporin A, ultraviolet A (UVA) and topical Doxepin, for treatment of the associated symptom of pruritis (itch), but the risk-to-benefit ratios for these agents are unfavorable for most of the conditions described above.

As a result, there is a significant and very long-standing need to identify new agents with favorable benefit to risk ratios that can be applied topically or given systemically to prevent or suppress (i.e. "treat") atopic dermatitis and its associated symptom of itch (pruritis). Optimally, such agents should be effective when administered locally or systemically, and systemic absorption should not result in blood levels high enough to cause significant systemic toxicity or other adverse side effects.

There are several conditions related to atopic dermatitis, such as hayfever, asthma and rheumatoid arthritis. It would be useful to have a method that treats these disorders as well as atopic dermatitis.

It is therefore an object of the present invention to provide methods for treating atopic dermatitis and pruritis.

It is another object of the present invention to provide methods for systemic treatment of atopic dermatitis and pruritis.

It is yet another object of the present invention to provide method for topical or transdermal treatment of atopic dermatitis and pruritis.

It is still a further object of the present invention to provide a method for treating conditions related to atopic dermatitis, such as hayfever, asthma, and rheumatoid arthritis.

SUMMARY OF THE INVENTION

A method for the treating atopic dermatitis and pruritis in a human or other mammal is disclosed that includes the administration of an effective amount of buspirone or its derivative or pharmaceutically acceptable salt, optionally in a pharmaceutically-acceptable diluent or carrier. The treatment can be used for atopic dermatitis occurring in any area of skin or in the eye. Additionally, patients with atopic dermatitis have a tendency to develop asthma, hay fever and rheumatoid arthritis. These related conditions can also be treated with buspirone or its derivative or a pharmaceutically-acceptable salt. In a preferred embodiment for the treatment of asthma, hay fever, and rheumatoid arthritis, buspirone or its derivative or a pharmaceutically-acceptable salt is administered intranasally or via an inhalation aerosol.

In one embodiment, buspirone or its derivative or salt is administered systemically, and preferably orally or transdermally, to relieve the symptoms of atopic dermatitis, the related conditions of asthma, rheumatoid arthritis and hayfever, and pruritis. The active agent can be administered in any dosage that achieves the desired result. Systemic dosages of between 0.05 and 25 mg/kg, and more preferably, between 0.1 and 2.5 mg/kg are typically useful for all of the described indications. The dosages can be given at any appropriate interval, and typically between once every several days to up to several times a day.

In an alternative embodiment, buspirone or its salt, free base form, or derivative is administered topically or transdermally to alleviate the symptoms of atopic dermatitis, pruritis, hay fever, asthma, and rheumatoid arthritis. The active agent can be administered in any appropriate topical composition, including in an ointment, gel, cream, lotion, suspension, ointment, tincture, spray, powder, paste, slow-release transdermal patch, aerosol, suppository for application to rectal, vaginal, nasal or oral mucosa, mouthwash, swish and spit preparation, inhaled aerosols, or intranasal preparations.

The active agent can be administered topically or systemically to treat the symptoms and pathology of ocular atopic dermatitis or pruritis. The active agent can be administered to eye tissue, for example, in an inert vehicle by intraocular injection or topically. The term "inert vehicle" refers to any vehicle that is inert to both the active agent and to the host, and includes adjuvants, preservatives, buffers, and demulcents. The active agent can be administered to nasal passages to treat asthma or hayfever, for example, intranasally or via an intranasal aerosol.

[4.5][decane-7,9-dione] on tissue swelling associated with oxazolone-induced contact hypersensitivity reactions. Oxazolone was applied to both ears of all mice and the change in ear thickness was measured at a specified interval thereafter. Buspirone HCl (100 mg/mL) (Group B) or vehicle alone (Group A) was applied to the right ear of Balb/c mice 2 hour after challenge. The change in ear thickness (post-challenge value minus baseline pre-challenge value) was measured 24 hours after oxazolone challenge. The data are presented as the mean±SEM (standard error of the mean). The reduction in ear swelling observed with 100 mg/mL buspirone HCl was significant when compared to the reactions observed in the control animals (Group A) (**=p<0.01).

Figure 1:
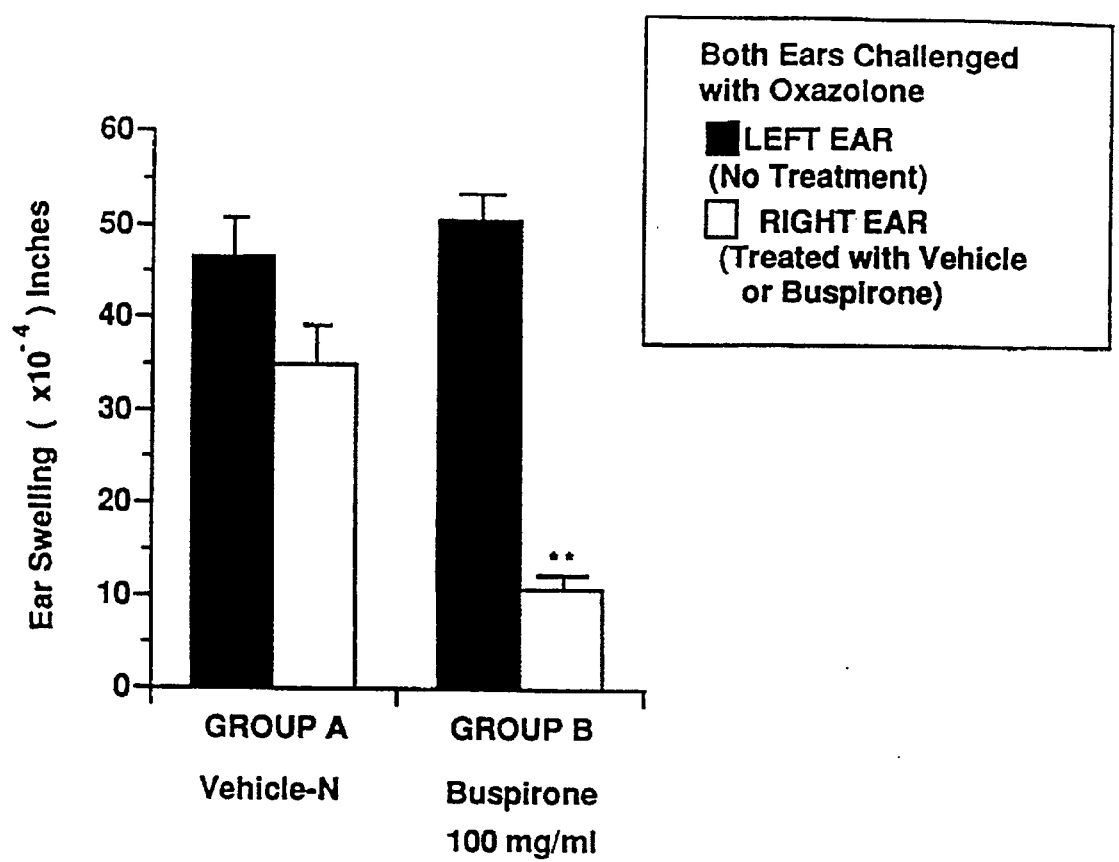
FIG. 1—Effect of topically administered buspirone HCl [(8-[4-[4-(2-pyrimidinyl)-1-piperazinyl]butyl]-8-azaspiro
Figure 2:
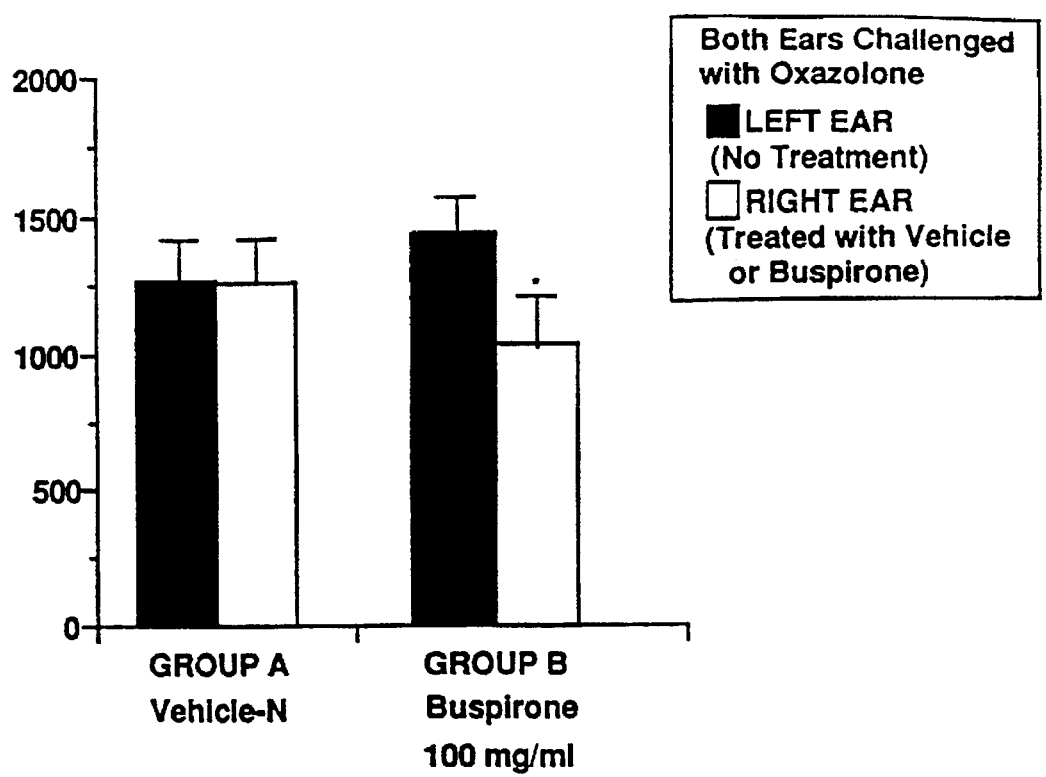

FIG. 2—Effects of topical treatment with 100 mg/kg buspirone HCl on leukocyte infiltration associated with 24-hour contact hypersensitivity reactions. These data (mean±SEM) are derived from the same mice whose ear thickness values are shown in FIG. 1. The reduction in leukocyte infiltration observed in animals treated with 100 mg/kg buspirone HCl was significant when compared to the reactions observed in animals treated with vehicle alone (*=p<0.05).

Figure 3:
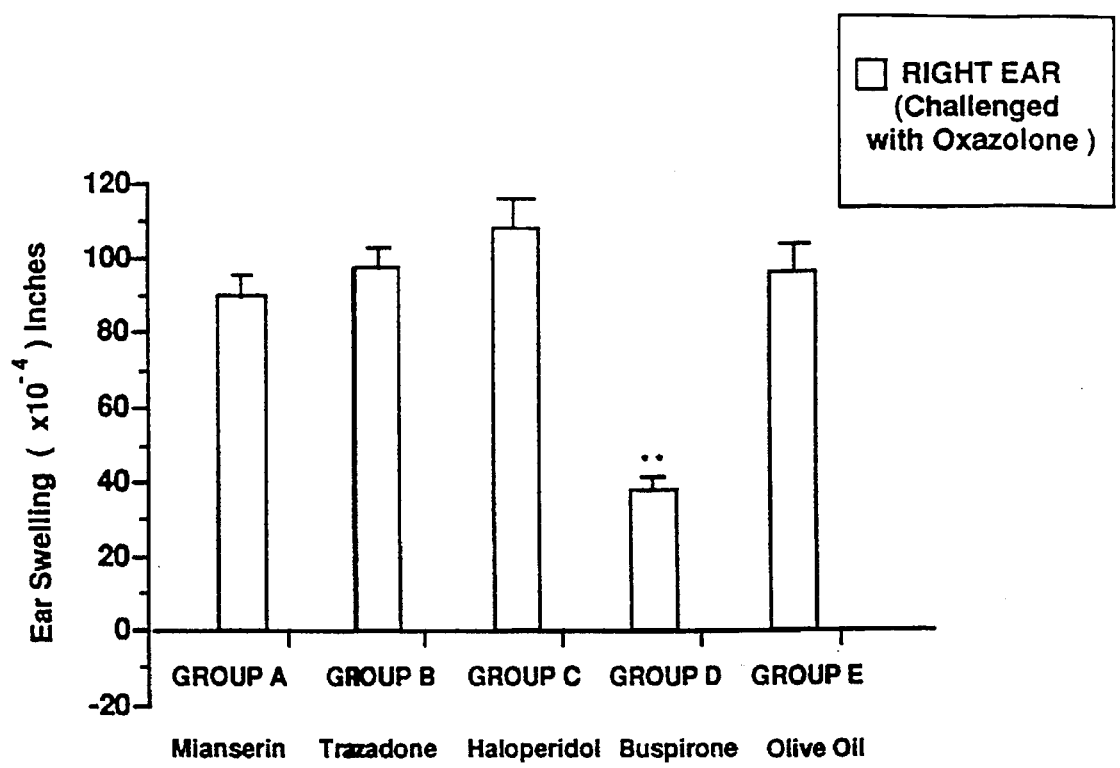

FIG. 3—Comparative effects of mianserin HCl (Group A), trazadone HCl (Group B), haloperidol (Group C), buspirone HCl (Group D), and systemic vehicle (Group E) (all agents administered subcutaneously at 50 mg/kg) on the tissue swelling associated with oxazolone-induced cutaneous contact hypersensitivity reactions. Buspirone HCl, the other agents, or vehicle alone were administered to BALB/c mice 1 hour after right ears only were challenged for contact hypersensitivity. The change in ear thickness (post-challenge value minus baseline pre-challenge value) was measured 24 hours after oxazolone challenge. The data are presented as the mean±SEM. The reduction in ear swelling observed with buspirone HCl was significant when compared to the reactions observed in the challenged right ears of control, vehicle treated animals (Group E) (**=p<0.01), whereas haloperidol, trazadone and mianserin did not significantly suppress the tissue swelling associated with contact hypersensitivity.

Figure 4:
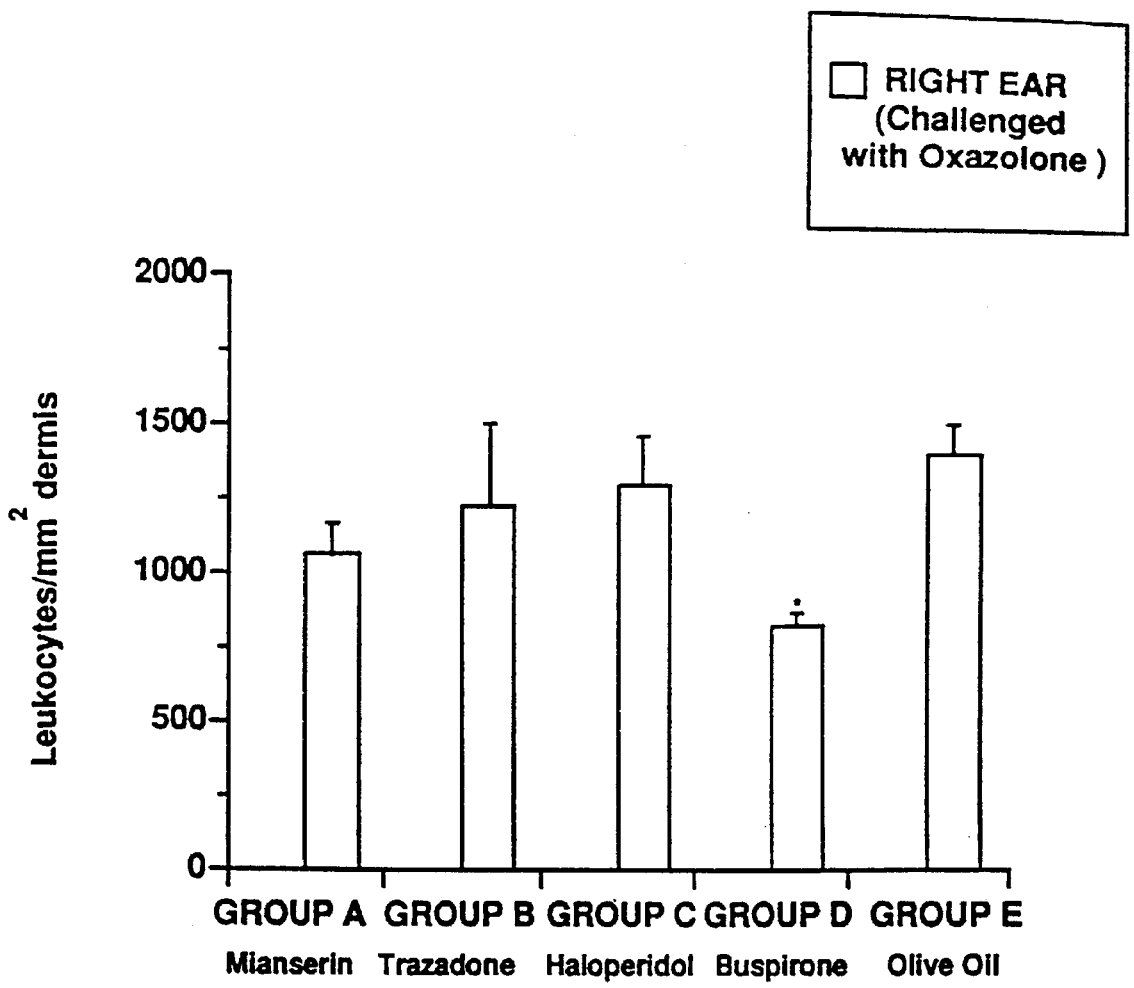

FIG. 4—Comparative effects of systemic treatment with mianserin HCl (Group A), trazadone HCl (Group B), haloperidol (Group C), buspirone HCl (Group D), and vehicle (Group E) (all agents administered subcutaneously at 50 mg/kg), on leukocyte infiltration associated with 24-hour contact hypersensitivity reactions. These data (mean±SEM) are derived from the same mice whose ear thickness values are shown in FIG. 3. The reduction in leukocyte infiltration observed in animals treated with buspirone HCl (Group D) was significant when compared to the reactions observed in animals treated with vehicle alone (Group E) (*=p<0.05), while haloperidol, trazadone HCl and mianserin HCl did not significantly suppress the leukocyte infiltration associated with contact hypersensitivity.

Figure 5A:
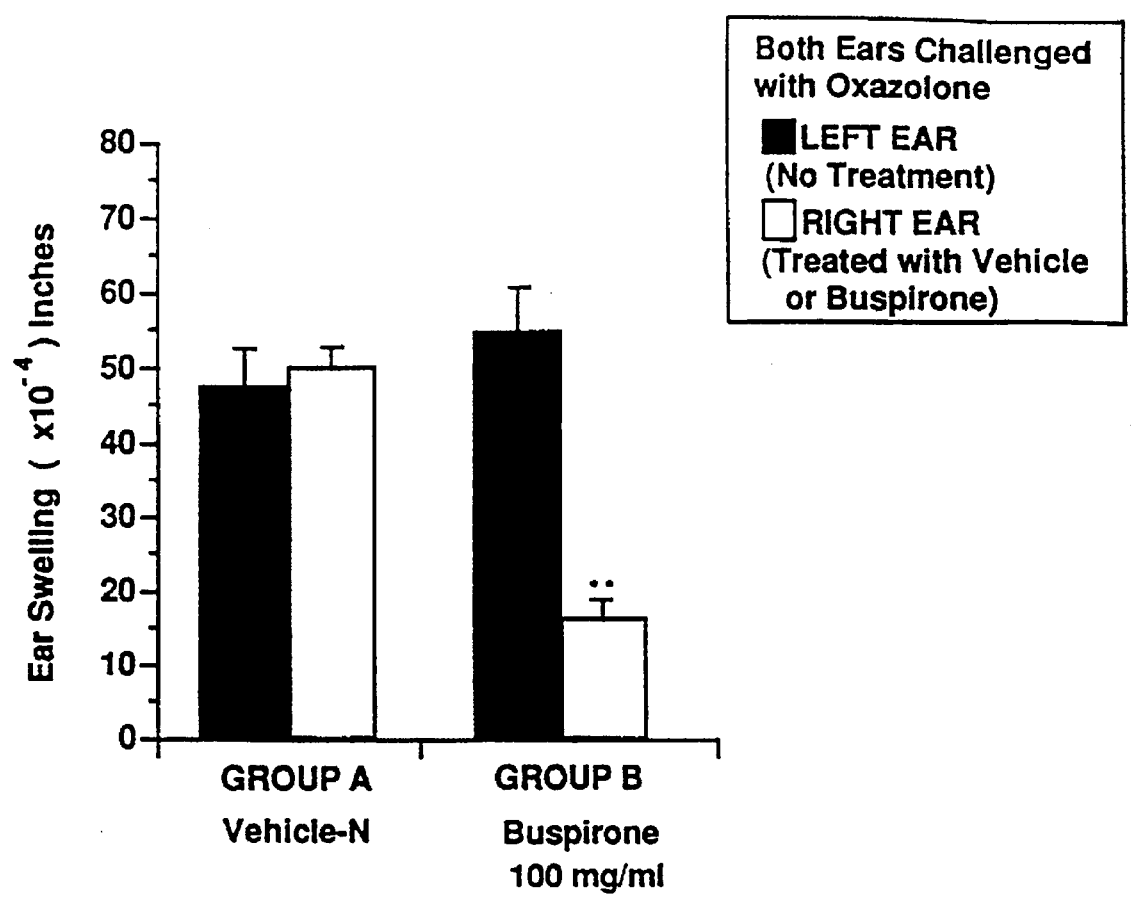

FIG. 5a,b—Effect of topically administered buspirone HCl on tissue swelling associated with oxazolone-induced contact hypersensitivity reactions. Oxazolone was applied to both ears of all mice at different times either pre- or post-buspirone HCl treatment, and the change in ear thickness was measured at a specified interval thereafter. a. Two hours before oxazolone challenge, 100 mg/mL buspirone HCl in Vehicle-N was applied to both surfaces of the right ears of (Group A) mice, whereas vehicle alone was applied to both surfaces of the right ears of the control (0% buspirone HCl Group B) animals. The ears were measured 24 hours after oxazolone challenge. Local pre-challenge treatment of the right ear with buspirone HCl significantly suppressed tissue swelling in the treated ear (p<0.01 vs contralateral oxazolone treated ears or vs right ears of vehicle treated group). Treating the right ear with 100 mg/mL buspirone HCl had no significant effect on the magnitude of swelling in the contralateral oxazolone treated ear. b. In a separate experiment, twenty-four hours after oxazolone challenge, 100 mg/mL buspirone HCl in Vehicle-N was applied to both surfaces of the right ears of Group B mice, whereas vehicle alone was applied to both surfaces of the ears of control Group A (0% buspirone HCl) mice. The change in ear thickness was determined 24 hours after treatment with buspirone HCl, i.e. at 48 hours after challenge with oxazolone. Treatment with buspirone HCl significantly diminished contact hypersensitivity reactions in the right ears of the treated animals (=p<0.01 when compared to the right ears in the control mice (Group A), and p<0.05 when compared to the contralateral ears of the same mice). The reactions in the left ears of the mice treated on the right ears with buspirone HCl (Group B) were not reduced when compared to reactions in the left ears of the vehicle-treated mice (Group A).

Figure 6A:
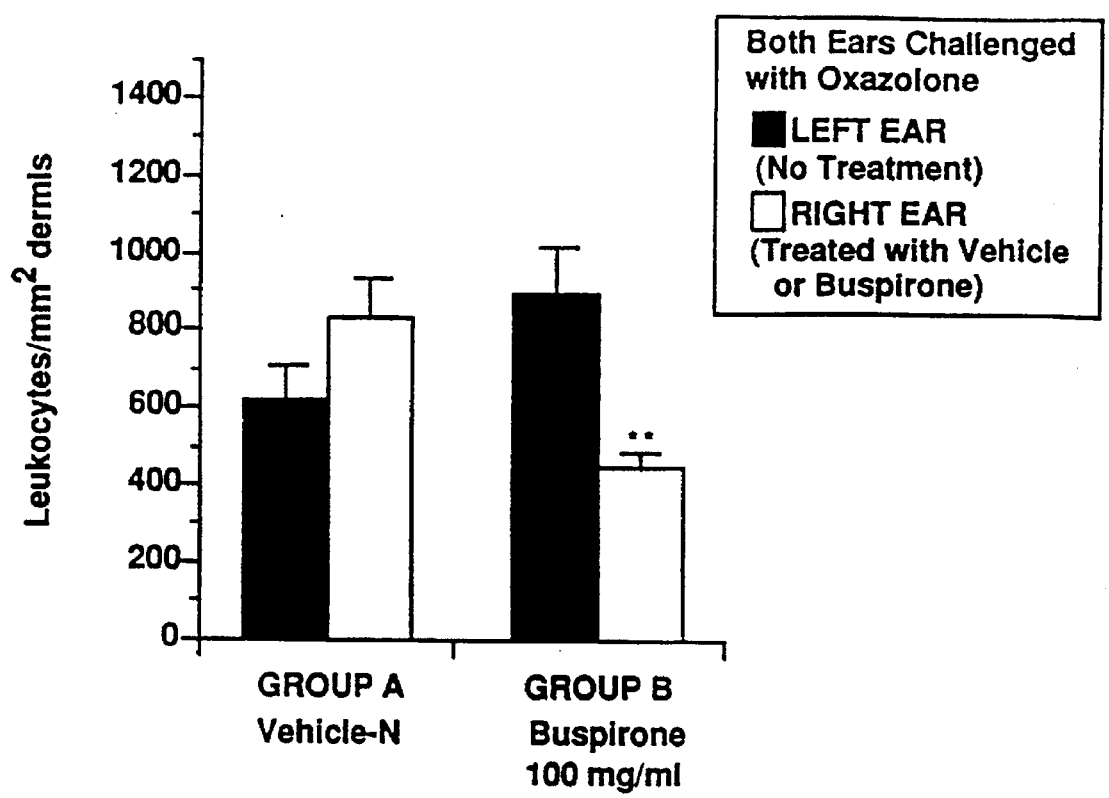

FIG. 6a,b—Effect of topical treatment with buspirone HCl on leukocyte infiltration associated with oxazolone-induced contact hypersensitivity reactions. These data (mean±SEM) are from the same mice whose ear thickness measurements are presented in FIG. 5a,b. Biopsies were performed 24 hours (a), or 48 hours (b) after application of oxazolone. Topical pre-challenge treatment with buspirone HCl significantly diminished the reactions when compared to those in vehicle-treated mice (6a) (=p<0.01), as did topical post-challenge treatment (6b) (=p<0.01).

Figure 7:
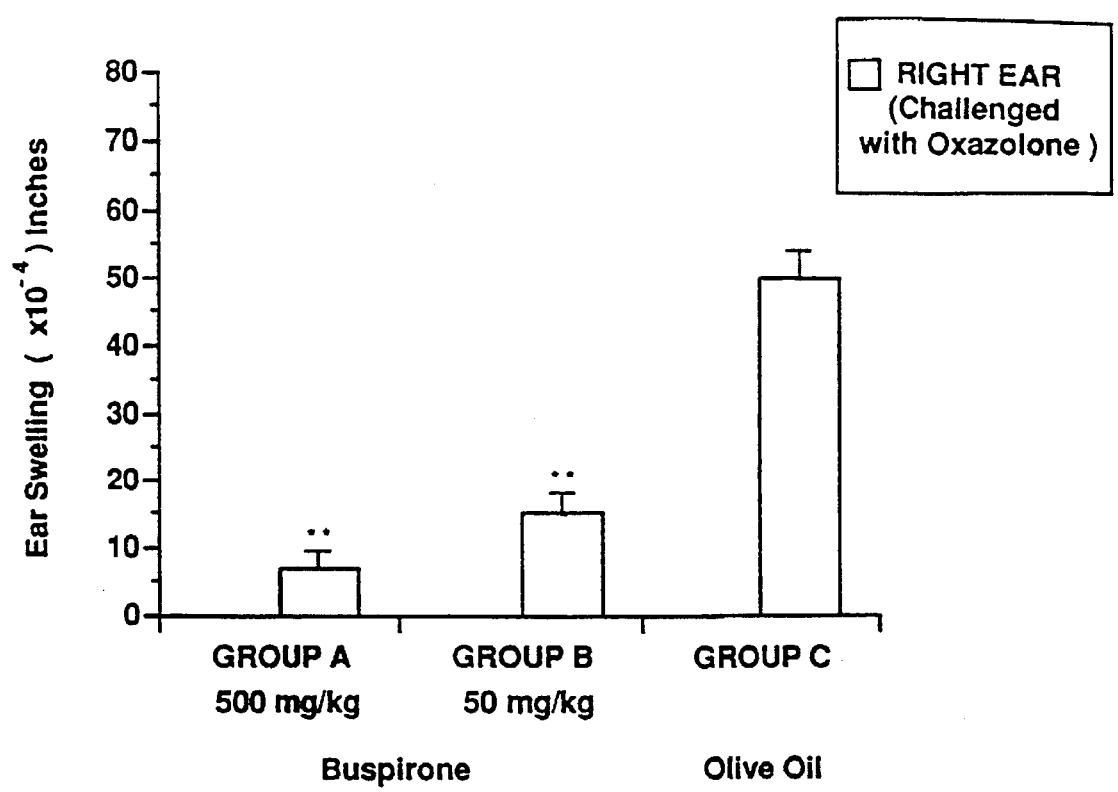

FIG. 7—Effect of systemic buspirone HCl (Group A, 500 mg/kg; Group B, 50 mg/kg) administered subcutaneously on tissue swelling associated with oxazolone induced cutaneous hypersensitivity reactions of the right ear. Buspirone HCl (Groups A and B) or vehicle alone (Group C) was administered to Balb/c mice 1 hour after challenge. Change in ear thickness (post-challenge—base line pre-challenge value) was measured 24 hours after oxazolone challenge. The data are presented as ±SEM.

Figure 8:
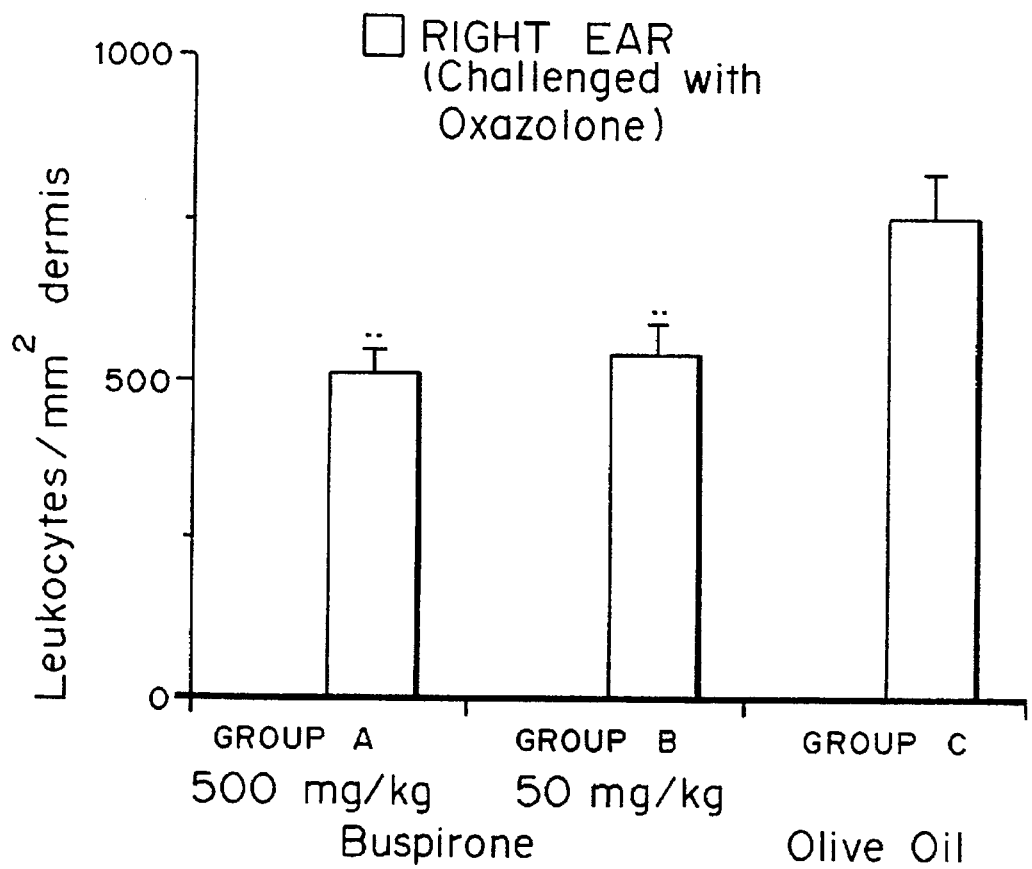

FIG. 8—Effect of systemic buspirone HCl (500 or 50 mg/kg buspirone HCl, administered subcutaneously) on leukocyte infiltration associated with oxazolone induced cutaneous hypersensitivity reactions of the right ear. These data are derived from the same mice whose ear thickness values are shown in FIG. 7. Systemic treatment with buspirone HCl (at 500 or 50 mg/kg) significantly reduced the leukocyte infiltration when compared to the reaction observed in animals treated with vehicle alone (**=p<0.01 for both Group A and Group B).

Figure 9:
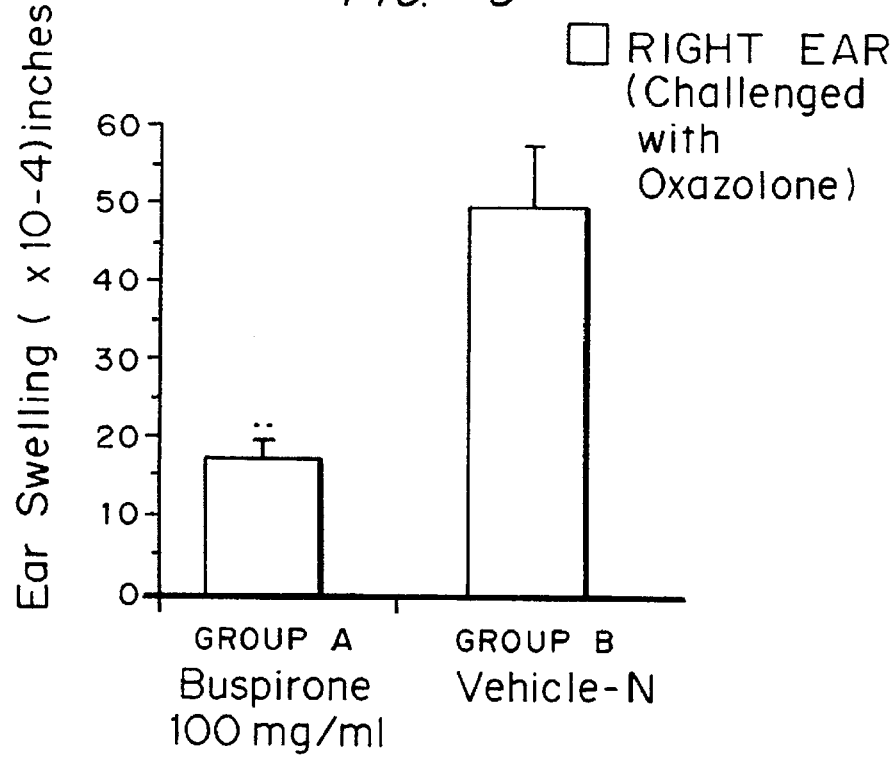

FIG. 9—The effect of topical treatment with buspirone HCl in suppressing the sensitization phase of oxazolone challenge. Buspirone HCl at 100 mg/mL (Group A) or vehicle-N (Group B) was applied to abdomen of mice 3 days prior to sensitization of Balb/c mice with 4% oxazolone. This treatment was repeated 3 days after sensitization. The right ears of all mice were then challenged with 0.5% oxazolone. The change in the ear thickness was measured 24 hours after oxazolone challenge. The data are presented as the mean±SEM. The reduction in ear swelling observed with buspirone HCl treatment (Group A) was significant when compared to those treated with vehicle only (Group B). (**=p<0.01).

Figure 10:
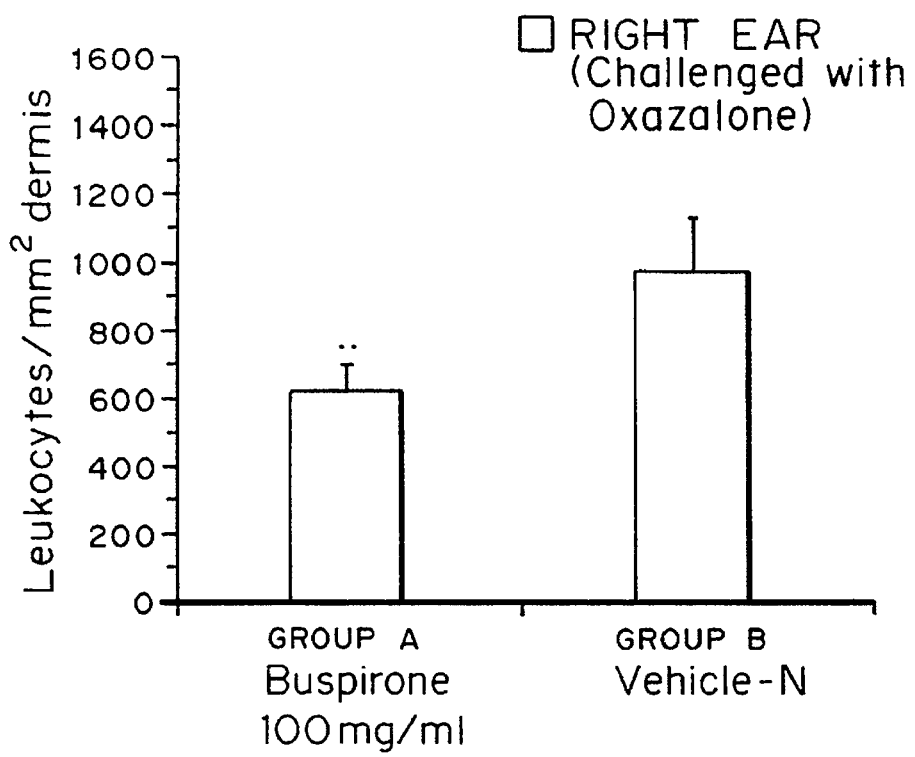

FIG. 10—Effect of topical treatment with buspirone HCl (100 mg/mL) on leukocyte infiltration associated with suppression of sensitization phase of oxazolone challenge. These data are from the same mice whose ear thickness measurements are presented in FIG. 9. Biopsies were performed 24 hours after oxazolone challenge. Topical buspirone HCl, administered both pre- and post-sensitization (Group A), significantly diminished the reactions as compared to the vehicle-only treated mice (Group B). (**= p<0.01).

Figure 11:
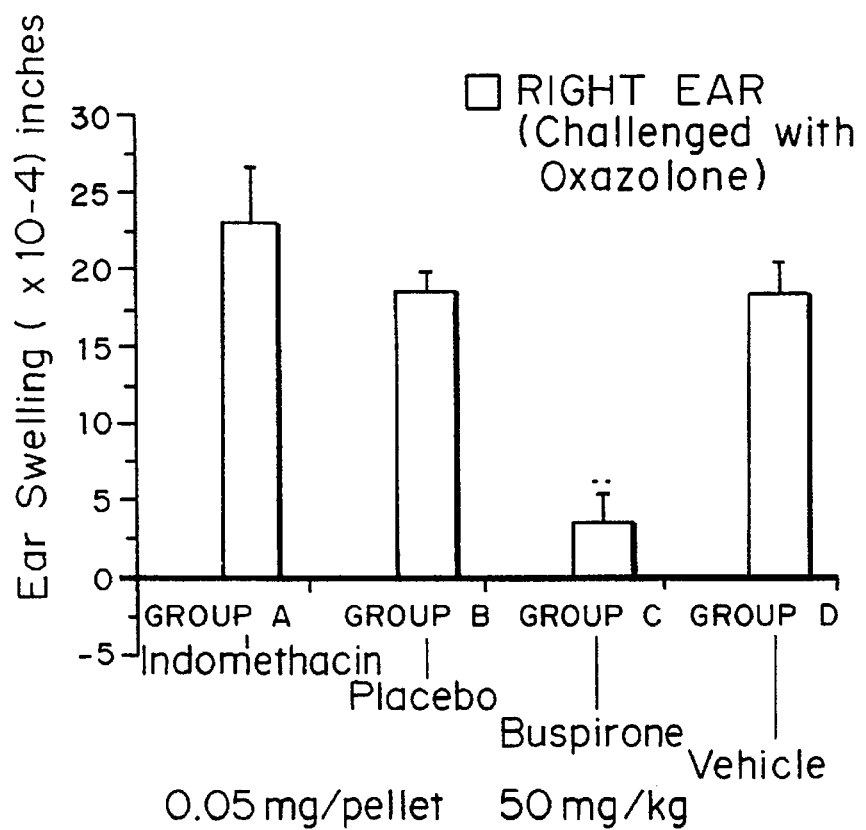

FIG. 11—Effect of systemic buspirone HCl treatment (50 mg/kg, administered subcutaneously), indomethacin, or placebo pellets (0.05 mg/pellet, implanted subcutaneously) on oxazolone induced contact hypersensitivity. Four groups of mice were sensitized to oxazolone by treatment with 4% oxazolone. Three days later two groups were implanted with 0.05 mg indomethacin (Group A) and placebo pellets (Group B). Three days later, right ears of mice in all four groups were challenged with 0.5% oxazolone. One hour post challenge, remaining two groups were treated with buspirone HCl at 50 mg/kg (Group C) or vehicle (Group D). Ear swelling was measured 24 hours after oxazolone challenge. Pre-challenge treatment with indomethacin or placebo (Groups A and B, respectively) did not have a significant effect on the hypersensitivity response as compared to control (Group D) in which vehicle alone was administered post-challenge. However, buspirone HCl treatment (Group C), applied post-challenge, significantly reduced ear swelling as compared to the control group (Group D, vehicle only). (**=p<0.01).

Figure 12:
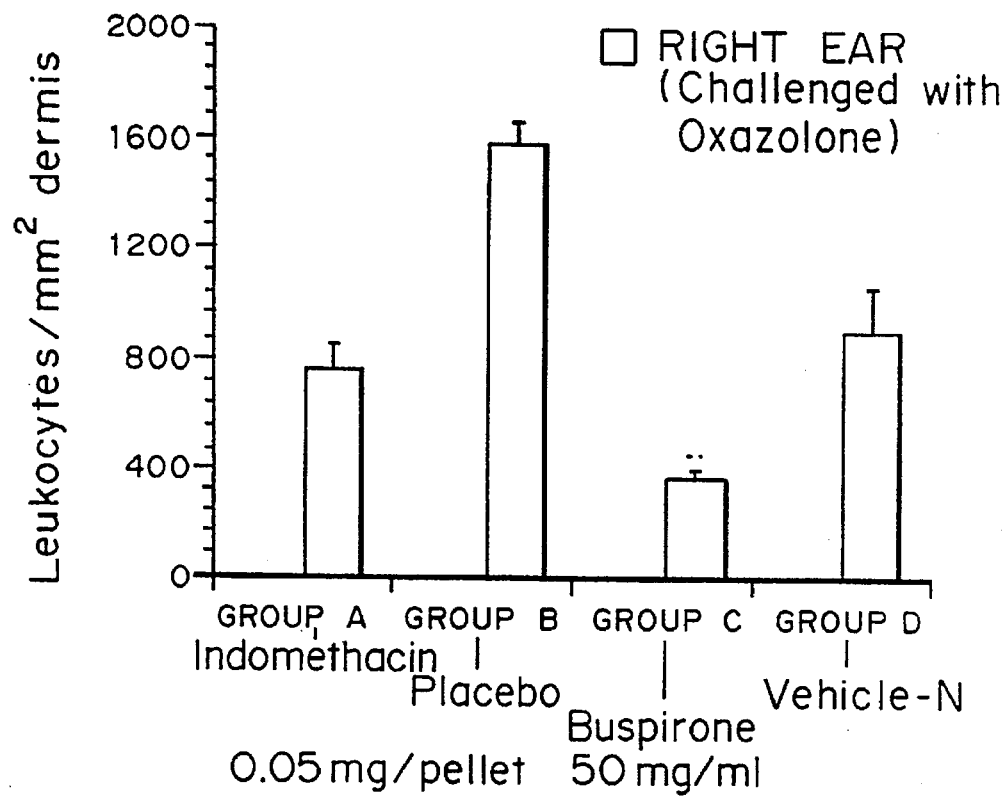

FIG. 12—Effect of systemic buspirone HCl treatment (Group C), indomethacin or placebo treatment (Groups A and B, respectively) on leukocyte infiltration associated with oxazolone induced cutaneous hypersensitivity reaction. These data are from the same mice whose ear thickness measurements are presented in FIG. 11. Biopsies were performed 24 hours after oxazolone challenge. Buspirone HCl treatment (Group C) significantly reduced leukocyte infiltration as compared to the control group (Group D, vehicle only) (**=p<0.01); whereas indomethacin and placebo treatment had no significant effects, when compared to the control group (Group D).

Figure 13:
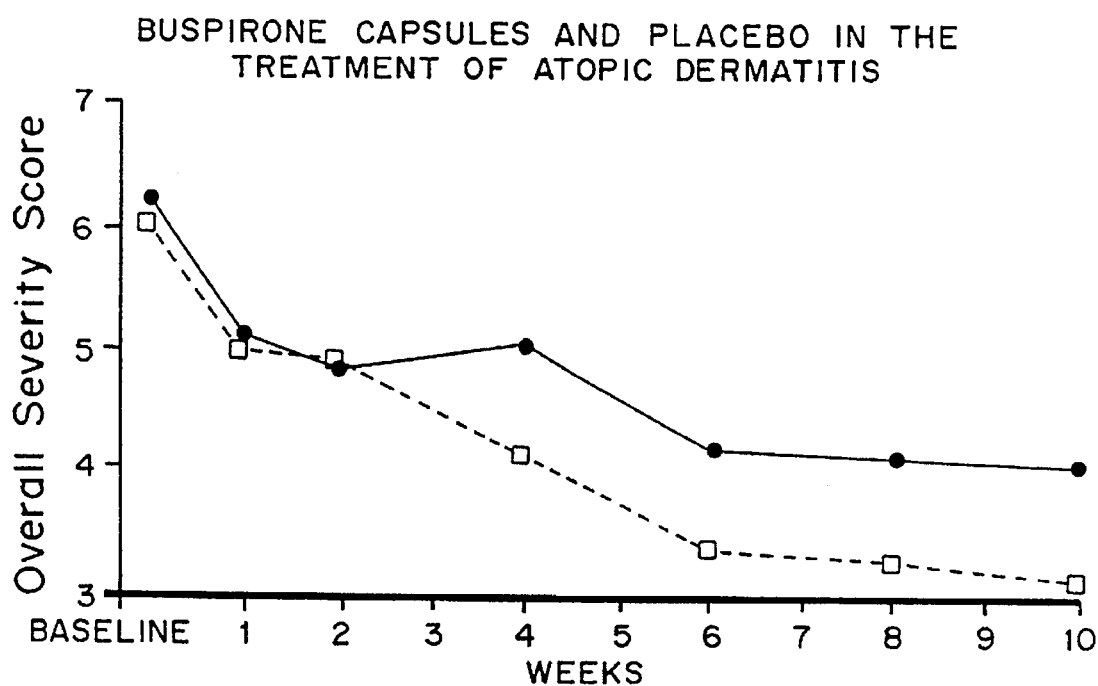

FIG. 13 is a graph illustrating the severity of atopic dermatitis (on a scale of 3 to 7) versus the number of weeks of systemic treatment with buspirone HCl. Solid circles represent treatment with a placebo. Empty circles represent treatment with buspirone HCl.

DETAILED DESCRIPTION OF THE INVENTION

Methods for treating atopic dermatitis and the related conditions of asthma, rheumatoid arthritis, hayfever and pruritis in a human or other mammal is disclosed that includes administering an effective amount of buspirone or a buspirone derivative or a pharmaceutically acceptable salt thereof, optionally in a pharmaceutically-acceptable diluent or carrier for systemic or topical application.

The parent buspirone [(8-[4-[4-(2-pyrimidinyl)-1-piperazinyl]butyl]-8-azaspiro[4.5][decane-7,9-dione] has neuroleptic or anxiolytic properties when administered systemically. The systemic neuroleptic or anxiolytic properties do not appear to adversely affect the patient regimen for treatment of atopic dermatitis. The neuroleptic or anxiolytic effects are not typically observed when buspirone is administered topically.

I. Buspirone and its Derivatives

The term alkyl, as used herein, unless otherwise specified, refers to a saturated straight, branched, or cyclic hydrocarbon of $C_1$ to $C_{20}$, including methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl.

The term aryl, as used herein, and unless otherwise specified, refers to phenyl or substituted phenyl, wherein the substituent is independently halo, alkyl, or oxy(alkyl) (for example, methyoxy, ethoxy, etc.), and wherein the aryl can have up to three substituents.

The term heterocycle refers to a cyclic moiety that has O, S, or N in the aromatic ring, including but not limited to, pyrryl, furyl, pyridyl, thiophene, pyrimidyl, thienyl, isothiazolyl, imidazolyl, tetrazolyl, pyrazinyl, pyrimidyl, quinolyl, isoquinolyl, benzothienyl, isobenzofuryl, pyrazolyl, indolyl, purinyl, carbozolyl, and isoxazolyl and the like, optionally substituted with halo (Cl, Br, I, or F), alkyl, oxyalkyl, aryl or oxyaryl.

The term aralkyl refers to an aryl group with an alkyl substituent.

The term alkaryl refers to an aryl group that has an aryl substituent.

The term alkene, as referred to herein, and unless otherwise specified, refers to an alkene group of $C_2$ to $C_{10}$, and specifically includes vinyl, and allyl.

As used herein, the ten "buspirone" refers to the compound (8-[4-[4-(2-pyrimidinyl)-1-piperazinyl]butyl]-8-azaspiro-[decane-7,9-dione).

As used herein, the term "buspirone derivative" refers to (1) a molecule of the formula:

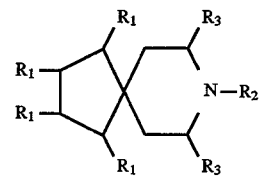

wherein:

$R_1$=H; halo (chloro, bromo, fluoro, or iodo); alkyl, specifically including $CH_3$—, cyclohexyl, $(CH_3)_2CH$—, $CH_3(CH_2)_3$—, $(CH_3)_2CHCH_2$—, $CH_3CH_2CH(CH_3)$—, $(CH_3)_3C$—, and —$CH_3(CH_2)$ p; Y—$CH_2(CH_2)_n$—; oxyalkyl; or aryl, specifically including $C_6H_5$—, (2, 3, or 4)—($OCH_3$) $C_6H_4$— and (2, 3, or 4)-($CH_3$)$C_6H_4$-; 2-X-$C_6H_4$-, 3-X-$C_6H_4$-, or 4-X-$C_6H_4$-; oxyaryl; or alkaryl;

$R_2$=H, $C_6H_5CH(CH_2CH_3)CH_2$-, $C_6H_5CH(CH_3)(CH_2)_2$-, $C_6H_5CH_2CH(CH_3)CH_2$-, $C_6H_5CH_2CH_2CH(CH_3)$-, $C_6H_5CH(CH_3)(CH_2)_3$-, (2, 3, or 4)-(alkyl)-$C_6H_4CH(CH_3)$ $(CH_2)_3$—, (2, 3, or 4)-(alkyloxy)-$C_6H_4CH(CH_3)(CH_2)_3$, (2, 3, or 4)-X-$C_6H_4$-alkyl, specifically including (2, 3, or 4)-X-$C_6H_4CH(CH_2CH_3)CH_2$-, (2, 3, or 4)-X-$C_6H_4CH(CH_3)$ $(CH_2)$ -, 4 -X-$C_6H_4CH(CH_3)(CH_2)_2$-, and 4-X-$C_6H_4$-CH $(CH_3)(CH_2)_3$-; $C_6H_5CH(OCH_3)(CH_2)_2$-,

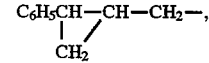

$C_6H_5CO(CH_2)_3$-, $C_6H_5CO(CH_2)_n$-, (2, 3, or 4)-(alkyl)-$C_6H_4CO(CH_2)_3$-, (2, 3, or 4)-(alkyl-oxy)-$C_6H_4CO(CH_2)_3$-, (2, 3, or 4)-X-$C_6H_4CO(CH_2)_n$-, 2-thienyl-CO-$(CH_2)_3$-, -alkyl-piperazinylaryl; -alkyl-$C_{3-8}$cycloalkyl-aryl; -alkyl-piperazinyl-heterocycle; -alkyl-$C_{3-8}$cycloalkyl-heterocycle; -alkyl-$C_{3-8}$cyclohexyl-Aryl$^1$; -alkyl-piperazinyl-Ar$^1$; -alkenyl-piperazinyl-aryl; -alkenyl-$C_{3-8}$cycloalkyl-aryl; -alkenyl-$C_{3-8}$cyclohexyl-Aryl$^1$; -alkenyl-piperazinylheterocycle; -alkenyl-$C_{3-8}$cycloalkyl-heterocycle; -alkenyl-piperazinyl-$Ar^1$;

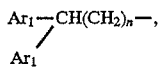

(2, 3, or 4)-$X-C_6H_4C(CH_3)CH(CH_2)_2$-, where the conformation about the double bond is cis or trans, (2, 3, or 4)-$X-C_6H_4C(CH_3)CHCH_2$-, where the conformation about the double bond is cis or trans, (2, 3, or 4)-$X-C_6H_4COCH=CHCH_2$-, $Y-CH_2(CH_2)_n$-, $Ar_1-(CH_2)_n$-, $C_1$ to $C_{20}$ alkyl, $X-(CH_2)_nCO$-, or $X-(CH_2)_n$-; R3 is $=O$, $=NH$, $=S$, chloro, bromo, iodo, fluoro, alkyl, or aryl;

n=1 to 6;

p is 1 to 20;

X=is independently F, Cl, Br, I, $OCH_3$, $SO_3$—, $NH_2$, H, —OH, —COOH, —COOR, —$SO_3H$, —CN, —$NHSO_3H$, —$NO_2$, or —$SO_2NH_2$;

Y=H, F, Cl, Br, I, —$SO_3$, —$PO_4^=$, —OH, —SH, —$SCH_3$, —$CH_3SO_2^-$, —$NH_2$, or —$CO_2^-$; and $Ar_1$ is, independently, aryl, (2, 3, or 4-$X-C_6H_4$-), (2, 3, or 4)-$(CH_2X)C_6H_4$-, (2, 3, or 4)-$(CX_3)C_6H_4$-, (2, 3, or 4)-$(CHX_2)C_6H_4$-, 2-thienyl, or (2, 3, or 4) -$X-C_6H_4CH_2$-;

or its pharmaceutically acceptable salt, including any quaternary salt known by those in the art, and specifically including the quaternary ammonium salt of the formula —$NR_3^{+Z-}$, wherein R is alkyl or benzyl, and Z is a counteranion, including chloride, bromide, iodide, -O-alkyl, toluenesulfonate, methylsulfonate, sulfonate, phosphate, or carboxylate (such as benzoate, succinate, acetate, glycolate, succinate, maleate, malate, citrate, tartrate, ascorbate, benzoate, cinnamoate, mandeloate, benzyloate, myristate, palmitate, stearate, oleate, palmitoleate, linoleate, linolenate and diphenylacetate).

I. Structure and Synthesis of Buspirone Derivatives

The parent buspirone is 8-[4-[4-(2-pyrimidinyl)-1-piperazinyl]butyl]-8-azaspiro[4.5]decane-7,9-dione, which has the structure illustrated below.

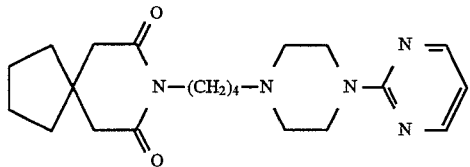

As demonstrated in Example 1, the parent buspirone has significant immunosuppressive activity. However, uncomplexed or unmodified buspirone also has significant anxiolytic effect when administered systemically. In one embodiment, buspirone is complexed, chemically modified, or provided in a formulation in such a manner that buspirone does not have an anxiolytic effect.

The potential utility of any one of the above-described forms of buspirone to treat atopic dermatitis can be conveniently determined by synthesizing the compound and testing it in the biological assay described in Example 1.

The quaternary salts described above can be prepared, for example, by reacting buspirone or a buspirone derivative with methyl chloride, methyl bromide, methyl iodide, methyl sulfate, methyl benzene-sulfonate, methyl p-toluenesulfonate, ethyl chloride, ethyl bromide, ethyl iodide, n-propyl chloride, n-propyl bromide, n-butyl bromide, isobutyl bromide, sec-butyl bromide, n-amyl bromide, n-hexyl chloride, benzyl chloride, benzyl bromide, and ethyl sulfate. Quaternary salt derivatives of buspirone have been found to be toxic to mice at elevated dosage levels, and therefore may not preferred buspirone derivatives.

Methods of synthesis of buspirone derivatives are disclosed in, or can be easily adapted from syntheses disclosed in We, et al., *J. Med. Chem.*, 15:477 (1972), Ger. Patent No. 2,057,845, and U.S. Pat. No. 3,717,634. See Also *J. Clin. Psychiat.*, 43:1–116 (1982), all of which are hereby incorporated by reference.

II. Complexation or Modification of the Buspirone Nucleus to Prevent Significant Anxiolytic Effect As discussed above, compounds with a buspirone nucleus that are effective at treating atopic dermatitis but that have a neuroleptic or anxiolytic effect can be complexed or modified to eliminate that effect, by one or more of the following processes.

A. Decreasing the Lipophilicity, equivalent to Increasing the Hydrophilicity of the Compound Buspirone derivatives that are effective at treating atopic dermatitis, yet also exhibit a neuroleptic or anxiolytic effect can be modified to minimize the neuroleptic or anxiolytic effect by decreasing the lipophilicity (equivalent to increasing the hydrophilicity) of the molecule. This can be done by adding one or more charged side chain(s) onto the molecule or by altering the existing side chain to make it more polar. The hydrophilicity of buspirone derivatives will in general increase when charged substituents are added.

B. Increasing the Size of the Molecule

Another technique for reducing the central nervous system (CNS) effects of compounds that contains a buspirone nucleus is to increase the size of the molecule via a covalent linkage to a large moiety (e.g., albumin or polyethylene glycol), using standard techniques of organic synthesis or by choosing a buspirone derivative with large substituents.

C. Complexing the Buspirone Nucleus with a Cyclic Molecule

A fourth method for reducing the central nervous system (CNS) effects, including anxiolytic effects, of a compound that contains a buspirone nucleus includes forming a non-covalent complex of the compound with a cyclic molecule such as a cycloamylose (e.g., a cyclodextrin such as β-cyclodextrin), which has a spatial arrangement of hydroxyl groups whereby the outer surface of the ring formed by the cycloamylose is hydrophilic and the inner surface is lipophilic.

When utilized in aqueous solution, this structure permits molecules (or parts thereof), termed "guest molecules", which are less polar than water and which are of suitable dimensions, to be incorporated into the lipophilic inner cavity, such that the cycloamylose/guest molecule complex presents to the blood-brain barrier as a relatively large and polar compound which is unable to penetrate the barrier. Such complexes may be prepared by any method known to the art, including those described in U.S. Pat. No. 4,555,504, which discloses β-cyclodextrin complexed with digoxin.

The efficacy of buspirone derivatives at treating or suppressing atopic dermatitis is related to the ability of the buspirone entity to function as an immunosuppressant. This ability can be tested in the assay described in Example 1 below. Whether the same entity is capable of inducing the neuropharmacological side effects observed for buspirone can be assayed by, for example, the hot plate test of Eddy et al., *J. Pharmacol.* 107:385 (1953) and 110:135 (1954), or by the method of Example 3.

The central nervous system side effects of a buspirone derivative can be estimated using molecular modeling and/or pharmacophore analysis. The dopamine and serotonin receptors are well characterized and strategies for estimating binding of drugs to these receptors are well established. For example, Schmidt, et al., *Molecular Pharmacology* 38:511–516 (1990), describe an algorithm for estimating the binding affinity of drugs to the 5-HT receptor. Also, a composite pharmacophore analysis and chemical database screening strategy is described by Sleight, et al, *Naunyn-Schmiedebergs Arch. Pharmacol.* 343:109–116 (1991), and Schmidt, A. W. and Peroutka, S. J., *Mol. Pharmacol.* 36(4): 505–511 (1989).

II. Therapeutic Compositions

Systemic Administration

In one embodiment, a buspirone or a buspirone derivative is administered systemically to treat atopic dermatitis and all of the other described indications. The buspirone or buspirone derivative can be administered subcutaneously, intravenously, intraperitoneally, intramuscularly, parenterally, orally, submucosally, by inhalation, intranasally, transdermally via a slow release patch, or topically, in an effective dosage range to cause immunosuppression.

Typical systemic dosages for all of the above-identified conditions are those ranging from between approximately 2 and 10 mg/kg per day as a single daily dose or divided daily doses.

The buspirone or buspirone derivative (the active compound) is administered for a sufficient time period to alleviate the undesired symptoms and the clinical signs, symptoms or pathologies associated with atopic dermatitis.

The active compound is included in the pharmaceutically acceptable carrier or diluent in an amount sufficient to deliver to a patient a therapeutic amount of compound of the buspirone derivative in vivo in the absence of serious toxic effects.

The concentration of active compound in the drug composition will depend on absorption, inactivation, and excretion rates of the drug as well as other factors known to those of skill in the art.

It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition.

Oral Administration

Oral administration is a preferred mode of systemic administration. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The buspirone or buspirone derivative or its salts can be administered as a component of an elixir, suspension, syrup, wafer, chewing gum or the like. A syrup may contain, in addition to the active compounds, sucrose as a sweetening agent and certain preservatives, dyes and colorings and flavors.

Intravenous Administration

If administered intravenously, preferred carriers are bacteriostatic water, physiological saline, Cremophor EL™ (BASF, Parsippany, N.J.) or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

The materials can also be obtained commercially from Alza Corporation and Nova Pharmaceuticals, Inc. Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations can be prepared by dissolving appropriate lipid(s) (such as stearoyl phosphatidyl ethanolamine, stearoyl phosphatidyl choline, arachadoyl phosphatidyl choline, and cholesterol) in an organic solvent that is then evaporated, leaving behind a thin film of dried lipid on the surface of the container. An aqueous solution of the buspirone derivative is then introduced into the container. The container is then swirled by hand to free lipid material from the sides of the container and to disperse lipid aggregates, thereby forming the liposomal suspension.

Topical Administration

In one embodiment, mammals, and specifically humans, suffering from atopic dermatitis and all of the other described indications can be treated by topically administering to the patient an effective amount of the buspirone or a buspirone derivative or its salt in the presence of a pharmaceutically acceptable carrier or diluent.

The active compound is included in the pharmaceutically acceptable carrier or diluent in an amount sufficient to deliver to a patient a therapeutic amount of the buspirone derivative in vivo in the absence of serious toxic effects. In general, local immunosuppression can be achieved by topically administering lower doses of buspirone derivatives than would be required if the agents were administered systemically. Typical dosages for topical application for all of the above-identified conditions are those ranging from 0.001% to 100% by weight of the active compound.

Suitable vehicles or carriers for topical application can be prepared by conventional techniques, such as lotions, suspensions, ointments, creams, gels, tinctures, sprays, powders, pastes, slow-release transdermal patches, suppositories for application to rectal, vaginal, nasal or oral mucosa, mouthwashes, or swish and spit preparations.

Buspirone or its derivative can be applied in a time release formulation via patches or by slow release polymers. The active compounds can be prepared with carriers that will protect the compound against rapid release, such as a controlled release formulation, including implants and microencapsulated delivery systems.

In addition to the other materials listed above for systemic administration, thickening agents, emollients, and stabilizers can be used to prepare topical compositions. Examples of thickening agents include petrolatum, beeswax, xanthan gum, or polyethylene glycol, humectants such as sorbitol, emollients such as mineral oil, lanolin and its derivatives, or squalene. A number of solutions and ointments are commercially available, especially for ophthalmic applications.

Natural or artificial flavorings or sweeteners can be added to enhance the taste of topical preparations applied for local effect to mucosal surfaces. Inert dyes or colors can be added, particularly in the case of preparations designed for application to oral mucosal surfaces.

Buspirone or its active derivatives can be provided as an ophthalmic drop or ophthalmic ointment to humans or other mammals, including dogs and cats, in an effective amount in a suitable vehicle. This topical ophthalmic treatment can treat manifestations in the eye that are associated with atopic dermatitis.

When used for ocular therapy, buspirone or its derivative salt can be administered in any convenient manner, including in an inert vehicle to eye tissue by intraocular injection or topically. The term "inert vehicle" refers to any vehicle that is inert to both the active agent and to the host, and can includes adjuvants, preservatives, buffers, and demulcents. As used herein, "ophthalmically effective amount" is that amount which in the composition administered and by the technique administered, provides an amount of therapeutic agent to the involved eye tissues sufficient to treat the disorder.

When the intraocular injection is subconjunctival, an ophthalmically effective amount of active agent can be, for example, administered typically in a polymeric carrier such as a dextran or polysorbate 80, which optionally contains additives such as disodium edetate, sodium sulfite, and/or sodium chloride, and sodium hydroxide or hydrogen chloride for pH adjustment. When the intraocular injection is intracameral or intravitreal, an effective amount of the active agent is typically administered in a vehicle containing phosphate buffered saline, citrate buffered saline, or chrondrotin sulfate, or in a polymeric vehicle such as sodium hyaluronate, or hyaluronic acid, purified polyacrylamide or polysorbate 80, with the formulation containing sodium hydroxide or hydrogen chloride for pH adjustment.

When the ocular administration is topical, a topical formulation containing an effective amount of the active agent is administered in a topically acceptable carrier. One example is an aqueous polymeric solution, aqueous suspension, ointment, gel or cream vehicle. Except for ointments, these vehicles may contain liposomes for creating a reservoir of dissolved agent for contact with the tear film.

Optional Components

Whether administered topically or systemically, the buspirone or buspirone derivative can also be mixed with other active materials which do not impair the desired action, or with materials that supplement the desired action, such as antibiotics, antifungals, anti-inflammatories, antivirals, or other immunosuppressive agents.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Administration of Buspirone or its Derivatives as Pharmaceutically Acceptable Salts Buspirone or its derivatives can be provided in the form of pharmaceutically-acceptable salts. As used herein, the term "pharmaceutically-acceptable salts or complexes" refers to salts or complexes that retain the desired biological activity of the parent compound and exhibit minimal, if any, undesired toxicological effects. Examples of such salts are (a) acid addition salts formed with inorganic acids (for example, hydrochloric acid, hydrobromic acid, sulfuric acid, phosphoric acid, nitric acid, and the like), salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acids, naphthalenedisulfonic acids, and polygalacturonic acid, and salts formed from fatty acids such as myristic acid, palmitic acid, stearic acid, palmitoleic acid, oleic acid, linoleic acid and linolenic acid; (b) base addition salts formed with polyvalent metal cations such as zinc, calcium, bismuth, barium, magnesium, aluminum, copper, cobalt, nickel, cadmium, and the like, or with an organic cation formed from N,N-dibenzylethylene-diamine or ethylenediamine; or (c) combinations of (a) and (b); e.g., a zinc tannate salt or the like.

Preferably, the pharmaceutically acceptable salt is a salt of buspirone or its derivatives and a fatty acid or sulfuric acid.

Modification of Buspirone or Buspirone Derivatives

The buspirone or buspirone derivatives can be modified in order to enhance their usefulness as pharmaceutical compositions. For example, it is well known in the art that various modifications of the active molecule, such as alteration of charge, can affect water and lipid solubility and thus alter the potential for percutaneous absorption. The vehicle, or carrier, can also be modified to enhance cutaneous absorption, enhance the reservoir effect, and minimize potential irritancy or neuropharmacological effects of the composition. See, in general, Arndt, K. A., P. V. Mendenhall, "The Pharmacology of Topical Therapy", *Dermatology in General Medicine*, 1987; T. B. Fitzpatrick, A. Z. Eisen, K. Wolff, I. M. Freedberg and K. F. Austen, eds., 3d ed., McGraw Hill, Inc., New York, pp. 2532–2540.

III. Immunosuppressant Activity of Buspirone Derivatives

Buspirone and buspirone derivatives are capable of acting systemically or topically to suppress the immune response in humans and other mammals.

Pathological immune responses that can be treated by topical application of buspirone or buspirone derivatives include atopic dermatitis, more particularly, eczematous dermatitis, ocular manifestations associated with atopic dermatitis, hay fever, asthma, and rheumatoid arthritis.

The ability of buspirone to influence the tissue swelling associated with contact hypersensitivity reactions in mice was evaluated as described in detail in Example 1. The parent buspirone compound was used for the procedure in Example 1 as a model of an active immunosuppressant. Buspirone derivatives can be measured against this model, and are considered active if they suppress the swelling response by at least 40% 24 hours after specific antigen challenge.

When applied topically, preparations of buspirone significantly suppressed the tissue swelling associated with the elicitation phase of contact hypersensitivity to oxazolone. However, mice treated topically with buspirone, unlike those treated systemically, exhibited no drowsiness or other evidence of central nervous system effects.

Buspirone expresses both serotonin and dopamine receptor antagonist activity. However, unlike buspirone, it was discovered that the chemically unrelated serotonin antagonists, trazadone and mianserin, and the dopamine receptor antagonist, haloperidol, were not effective in suppressing contact hypersensitivity. On the basis of this, it appears that the mechanism of action of buspirone on the immune response is independent of its serotonin or dopamine receptor blocking properties, and therefore, buspirone derivatives with immunosuppressive effect yet without neuroleptic or anxiolytic effect can be provided by the method of selection disclosed generally herein.

EXAMPLE 1

Inhibition of Induced Contact Hypersensitivity

Six-to-8-week-old female C57BL/6J or BALB/c mice were obtained from the Jackson Laboratory, Bar Harbor, Me. or from Charles River Laboratories, Kingston Facility, Stoneridge, N.Y., respectively. Buspirone HCl, mianserin, trazadone, haloperidol and oxazolone were purchased from the Sigma Chemical Co. (St. Louis, Mo.).

Oxazolone-Induced Contact Hypersensitivity—Sensitization and challenge for contact hypersensitivity were performed as follows. The abdomens of the mice were shaved with electric clippers, 50 µl of a 4% (w/w) solution of oxazolone in 4:1 (v:v) acetone:olive oil were applied to the shaved abdomen, and 5 µl of the same solution were applied to each hind footpad. Five to eight days later, the mice were challenged for contact hypersensitivity by applying 10 µl of a 0.5% (w:w) solution of oxazolone in 4:1 (v:v) acetone:olive oil to both the inner and outer surface of the right ear of each mouse (in the case of mice treated systemically with buspirone HCl) or to both ears (in the case of mice treated topically with buspirone HCl)—except in the case where sensitization phase suppression is studied, as in FIGS. 9 and 10.

Systemic Buspirone HCl Treatment—One hour after the application of oxazolone for elicitation of contact hypersensitivity, mice were treated subcutaneously with buspirone HCl 500 or 50 mg/kg body weight) in 0.1 mL of carrier (Cremophor EL, BASF, Parsippany, N.J.), or with 0.1 mL of carrier alone. In a separate experiment, mice were treated in a similar fashion with 50 mg/kg body weight of trazadone, mianserin, haloperidol, or buspirone HCl in 1 mL olive oil or with olive oil alone.

Topical Buspirone HCl Treatment For these experiments, both ears of each mouse were challenged for elicitation of contact hypersensitivity by the application of oxazolone (as appropriate) to both surfaces of both ears. Two hours before, or twenty-four hours after application of hapten, the right ears of some mice were treated with buspirone HCl in vehicle, applied epicutaneously to both surfaces. The tright ears of control mice were similarly treated, but with vehicle alone. In the case of experiments designed to assess topical effects on the sensitization phase, only the right ear is challenged. (See FIGS. 9 and 10)

Evaluation of Ear Swelling Response—Immediately before and 24 or 48 hours after application of oxazolone, ear thicknesses were determined with an engineer's micrometer. The increment (delta) in ear thickness (ear swelling) was calculated as the 24- or 48-hour value minus the baseline (pre-challenge) value and expressed in units of $10^{-4}$ inches.

Mice were killed by cervical dislocation after the measurement of 24-hour ear thickness was obtained, and the ears were processed for histologic examination.

Quantification of Leukocyte Infiltration—Both ears of each mouse were fixed in 4.0% buffered formalin and then processed routinely and embedded in paraffin for preparation of 6–7 µm-thick hematoxylin and eosin-stained sections. All of the sections were coded and examined with an ocular grid at 400× under light microscopy by an observer unaware of the identity of the individual slides. The number of leukocytes/mm$^2$ of dermis was calculated by counting all of the leukocyte cells in an area of at least 0.14 mm$^2$ of dermis.

Statistical Analysis—Differences between groups were assessed by the 2-tailed Student's t test (paired for comparisons of left and right ears in the same mice, unpaired for comparisons between different groups of mice).

Effect of Topical Buspirone HCl on Expression of Contact Hypersensitivity—FIGS. 1 and 2 illustrate the effect of topical application of 100 mg/mL of buspirone HCl (Group B) or carrier alone (Group A) on expression of contact hypersensitivity. As indicated, topical administration of buspirone HCl at 100 mg/mL significantly decreased ear swelling (FIG. 1) and aggregation of leukocytes (FIG. 2). Importantly, while topical application of buspirone HCl was extremely effective in diminishing both the tissue swelling and the leukocyte infiltration associated with contact hypersensitivity reactions, these effects were observed in the absence of detectable alterations in the behavior of the mice. The mice treated topically with buspirone HCl appeared active and retained apparently normal interest in food and water.

Effect of Systemic Buspirone HCl Versus Other Serotonin or Dopamine Receptor Antagonists—In these experiments, systemic buspirone HCl was compared to the serotonin receptor antagonists, trazadone or mianserin, and to the dopamine receptor antagonist, haloperidol, for their ability to inhibit cutaneous contact hypersensitivity. At a dose of 50 mg/kg, only buspirone HCl significantly reduced cutaneous contact hypersensitivity (FIGS. 3 and 4).

Figure 5B:
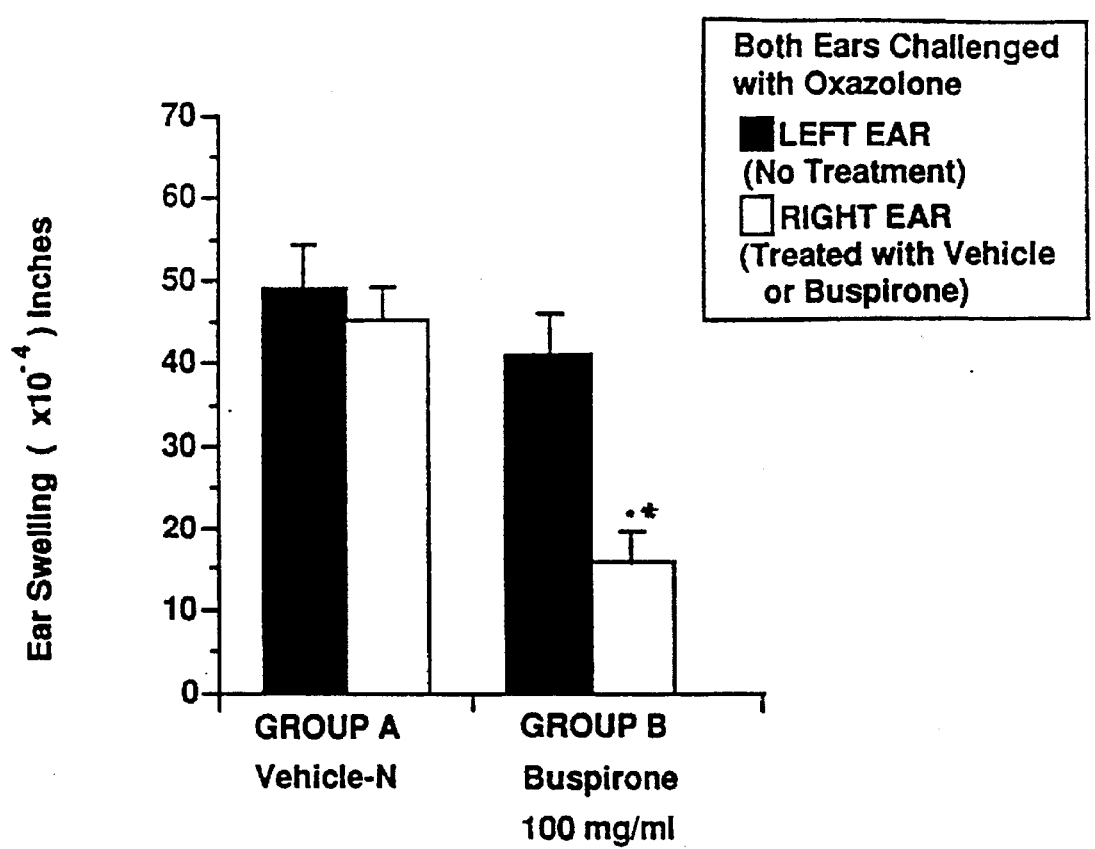
Figure 6B:
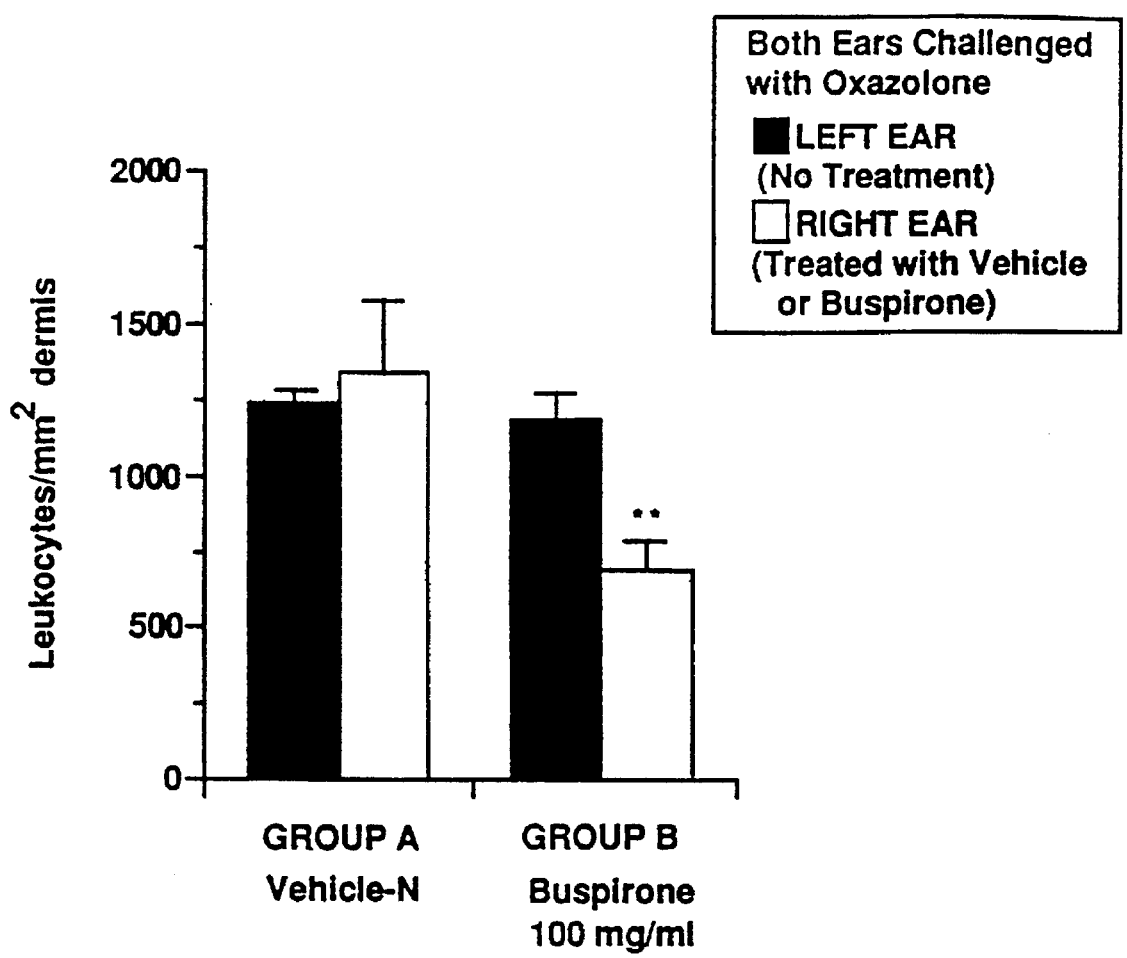

Effect of Topically Administered Buspirone HCl on Tissue Swelling Associated with Oxazolone-Induced Contact Hypersensitivity Reactions/Effect of Time of Administration of Topical Buspirone HCl. Oxazolone was applied to both ears of all mice at different times either pre- or post-buspirone HCl treatment, and the change in ear thickness was measured at a specified interval thereafter. a. Two hours before oxazolone challenge, 100 mg/mL buspirone HCl in Vehicle-N was applied to both surfaces of the right ears of some mice, whereas vehicle alone was applied to both surfaces of the ears of the control (0% buspirone HCl) animals. The ears were measured 24 hours after oxazolone challenge (FIG. 5a). Local pre-challenge treatment of the right ear with buspirone HCl significantly suppressed tissue swelling in the treated ear (**$p<0.01$ vs contralateral oxazolone treated ears or vs right ears of vehicle treated group). Treatment of the right ear with 100 mg/mL buspirone HCl had no significant effect on the magnitude of swelling in the contralateral oxazolone treated ear. b. In a separate experiment, twenty-four hours after oxazolone challenge, 100 mg/mL buspirone HCl in Vehicle-N was applied to both surfaces of the right ears of some mice, whereas vehicle alone was applied to both surfaces of the ears of control (0% buspirone HCl) mice. The change in ear thickness was determined 24 hours after treatment with buspirone HCl, i.e. at 48 hours after challenge with oxazolone (FIG. 5b). Treatment with buspirone HCl significantly diminished contact hypersensitivity reactions in the right ears of the treated animals (*=$p<0.01$ when compared to the right ears in the control mice, and $p<0.05$ when compared to the contralateral ears of the same mice). The reactions in the left ears of the mice treated on the right ears with buspirone HCl were not reduced when compared to reactions in the left ears of the vehicle-treated mice. When the ears of the same mice shown in FIGS. 5a and 5b were examined histologically (FIGS. 6a and 6b), buspirone HCl treatment was shown to diminish significantly the leukocyte infiltration associated with the contact hypersensitivity response (**=p<0.01 when compared to the right ears in the vehicle-tested mice).

Effect of Systemic Treatment with Buspirone HCl on Expression of Contact Hypersensitivity—The subcutaneous administration of buspirone HCl at dosages of 500 or 50 mg/kg, 1 hour after challenge markedly diminished the tissue swelling which developed in association with the contact hypersensitivity response (FIG. 7). The leukocyte infiltration associated with the response in mice treated with 500 or 50 mg/kg buspirone HCl was also diminished compared to responses in mice not treated with the drug (FIG. 8). However, at these dosages, buspirone HCl also produced other remarkable systemic effects. The mice rapidly became lethargic after administration of the drug, and, by 23 hours after buspirone HCl injection, the mice exhibited profound depression of central nervous system function (these effects were more pronounced in the high dosage group). They appeared to be in a deep sleep, neither ate nor drank, and responded weakly or not at all to touch. They did, however, exhibit responsiveness to pinch, in both dosages.

EXAMPLE 2

Comparison of Immunosuppressant versus Anti-inflammatory activity

Mice were sensitized to oxazolone as described in Example 1. Three days later, slow release indomethacin pellets (0.05 mg, 3 week release) were implanted subcutaneously under light ether anesthesia. The dose of indomethacin delivered by these pellets has been previously shown to completely block prostaglandin synthesis in mice, by Jun, D. D., et al., *J. Invest. Dermatol.* 90:311 (1988).

Three days later, mice were challenged for contact hypersensitivity as in Example 1. When the hypersensitivity response was assessed 24 hours later, indomethacin was shown to have no significant effect on the response. These FIGS. (11 and 12) show that a classic anti-inflammatory agent, indomethacin, does not appear to suppress the edema associated with the immunologically specific oxazolone induced contact hypersensitivity response and compared to buspirone HCl, only weakly suppresses the leukocyte infiltration associated with the response.

EXAMPLE 3

Evaluation of Serotonin Receptor Binding Activity or Dopamine Receptor Binding Activity of Buspirone Derivatives Buspirone derivatives which lack serotonin receptor binding or dopamine receptor binding activity can be identified as follows. A radiolabeled ligand known to bind serotonin and/or dopamine receptors can be bound to an appropriate substrate expressing one or both of these receptors. For example, radiolabeled quipazine which is available commercially can be used as the ligand. The buspirone derivative to be tested is then incubated with the radiolabeled quipazine ligand combination. Displacement of radiolabeled ligand is positive evidence that the buspirone derivative being tested can bind serotonin and/or dopamine receptors. The amount of radiolabeled ligand which is displaced is determined by an appropriate standard curve which can also provide information concerning binding affinities. The displaced radiolabeled ligand can be quantitated using a standard scintillation counter.

A detailed description of how to perform the binding studies using $^3$H-quipazine and the example follows:

Binding studies using $^3$H-quipazine are described in detail by Milburn, C. M. and Peroutka, S. J., *J. Neurochem.* 52:1787–1792 (1989). Briefly, rat cortices are homogenized in 20 volumes of 50 mM Tris HCl buffer pH 7.7 at 25° C. and centrifuged at 49,000×g for 10 min. The pellet is resuspended in fresh buffer and incubated at 37° C. for 10 min. After the final centrifugation, the pellet is resuspended in 80 volumes of Krebs-HEPES buffer (25 mM HEPES, 118 mM NaCl, 5 mM KCl, 2.5 mM $CaCl_2$, and 1.2 mM $MgCl_2$ pH adjusted to 7.4). Tissue (10 mg of original wet weight) is added to assay tubes containing 0.8 nM [$^3$H]quipazine and displacing drug or buffer in a final volume of 1 mL. Non-specific binding is defined using 1 micromole zacopride. After a 30 min incubation at room temperature, the tissue is rapidly filtered under vacuum through No. 32 glass fiber filters and rinsed twice with 5 mL of 50 mM Tris-HCl buffer pH 7.7. Radioactivity is quantified by liquid scintillation counting. All experiments are performed three to six times, each in triplicate. This same approach can be used with other radiolabeled ligands such as zacopride, granisetron, haloperidol, mianserin, ketanserin, 5-HT, dopamine, droperidol, or ritanserin.

EXAMPLE 4

Treatment of Atopic Dermatitis

The effectiveness of buspirone HCl at treating atopic dermatitis was evaluated. The evaluation was a randomized, double-blind, placebo-controlled study in which 40 subjects with moderate atopic dermatitis were assigned to receive systemic treatment with either placebo or buspirone HCl capsules (19 buspirone and 21 placebo).

The mean age of the patients was 39 years (range 19–77 years), the mean duration of atopic dermatitis was 12 years, and the percent BSA affected was 24%. The majority of the patients were female (55%), caucasian (72%), and with an arm (53%) as the target lesion.

Each patient treated with buspirone received one bottle of 48 buspirone HCl capsules containing 5 mg buspirone each. The initial dose was three capsules/day (15 mg/day buspirone HCl). The dosage was increased by one capsule/day on days 3, 5 and 7, at which point the targeted six capsule dosage (30 mg buspirone HCl/day) was reached. The daily dosage of 6 capsules/day (30 mg buspirone HCl/day) was maintained for the remainder of the eight-week treatment period.

A global evaluation was made for the improvement of all lesions compared to the baseline condition. Subjects also assessed the severity of pruritis daily using a visual analog scale in their diary cards. Atopic dermatitis severity was measured on a seven point scale (0.0=none, 1=mild, 2=moderate, and 3.0=severe, measured at 0.5 point increments. The target lesion to be evaluated had a baseline overall severity score of 4.0 to 7.0.

The primary efficacy endpoints included the pruritus score (scored on a 0–3 scale at 0.5 increments), the pruritus diary report (using a 100 mm analog scale), and the Overall Severity Score (sum of ratings for erythema, induration, and pruritus: each measured on a 0–3 scale at 0.5 increments); analysis was limited to comparisons within treatment groups. Efficacy evaluations were based on all eligible subjects receiving at least one week of study therapy. A carry-forward approach was used to account for subjects not completing therapy. A signed rank test was used to test for within group changes from baseline to the end of treatment.

For pruritus scored on a 0–3 scale, there were larger improvements following treatment for buspirone than for the placebo. The mean score at baseline was 2.13 for Buspirone versus 2.26 for Placebo (Table 1). At the end of treatment, the mean score was 1.37 for Buspirone, while the mean score was 1.67 for Placebo. The mean change from baseline to end of treatment was significant for Buspirone (0.76 improvement, p=0.0076) and for Placebo (0.60 improvement, p=0.0202). The pooled within-subject standard deviation of the Overall Severity Score was 0.97.

baseline to end of treatment was significant for buspirone (16 mm improvement, p=0.154) and for placebo (2 mm improvement, p=1.000).

TABLE I

Buspirone Capsules and Placebo in the Treatment Of Atopic Dermatitis
Summary of Individual Severity Scores - Pruritis

| | | Treatment | | | | | | |
|---|---|---|---|---|---|---|---|---|
| | | Buspirone | | | | Placebo | | |
| | | # | Mean | Std | p-value* | # | Mean | Std | p = value* |
| Baseline | Actual | 19 | 2.13 | 0.40 | | 21 | 2.26 | 0.44 | |
| Week 1 | Actual | 19 | 1.74 | 0.73 | | 21 | 1.74 | 0.64 | |
| | Change from Baseline | 19 | −0.39 | 0.77 | 0.0537 | 21 | −0.52 | 0.77 | 0.0054 |
| Week 2 | Actual | 18 | 1.78 | 0.75 | | 20 | 1.70 | 0.75 | |
| | Change from Baseline | 18 | −0.39 | 0.85 | 0.0933 | 20 | −0.55 | 0.81 | 0.0112 |
| Week 4 | Actual | 15 | 1.33 | 0.84 | | 17 | 1.68 | 0.85 | |
| | Change from Baseline | 15 | −0.77 | 0.95 | 0.0168 | 17 | −0.59 | 0.78 | 0.0107 |
| Week 6 | Actual | 14 | 1.00 | 0.76 | | 15 | 1.37 | 0.83 | |
| | Change from Baseline | 14 | −1.11 | 0.94 | 0.0024 | 15 | −0.97 | 0.69 | 0.0005 |
| Week 8 | Actual | 13 | 1.00 | 0.79 | | 16 | 1.34 | 0.93 | |
| | Change from Baseline | 13 | −1.12 | 0.98 | 0.0059 | 16 | −0.94 | 0.91 | 0.0022 |
| End of Treatment | Actual | 19 | 1.37 | 0.98 | | 21 | 1.67 | 1.04 | |
| | Change from Baseline | 19 | −0.76 | 1.11 | 0.0076 | 21 | −0.60 | 1.04 | 0.0202 |
| Week 10 | Actual | 14 | 0.79 | 0.80 | | 15 | 1.40 | 0.99 | |
| | Change from Baseline | 14 | −1.32 | 0.99 | 0.0017 | 15 | −0.93 | 0.96 | 0.0044 |
| | Change from End of Treatment | 14 | −0.21 | 0.67 | 0.3750 | 15 | 0.07 | 0.32 | 0.7500 |

For pruritus scored using a 100 mm analog scale, there were larger improvements following treatment for buspirone versus placebo. The mean score at baseline was 55 mm for buspirone versus 48 mm for placebo (Table 2). At the end of treatment, the mean score was 40 mm for buspirone, while the mean score was 44 for placebo. The mean change from

TABLE 2

Buspirone Capsules and Placebo in the Treatment of Atopic Dermatitis
Summary of Pruritis Visual Analog Scale - Carry forward

| | | Treatment | | | | | | |
|---|---|---|---|---|---|---|---|---|
| | | Buspirone | | | | Placebo | | |
| | | # | Mean | Std | p-value* | # | Mean | Std | p = value* |
| Baseline | Actual | 18 | 54.89 | 34.79 | | 18 | 47.61 | 26.33 | |
| Week 1 | Actual | 19 | 51.30 | 27.48 | | 20 | 50.06 | 20.46 | |
| | Change from Baseline | 18 | −3.90 | 23.58 | 0.3927 | 18 | 4.04 | 15.96 | 0.3465 |
| Week 2 | Actual | 19 | 48.83 | 31.32 | | 20 | 47.07 | 27.07 | |
| | Change from Baseline | 18 | −6.20 | 39.60 | 0.6705 | 18 | 1.79 | 22.62 | 0.5171 |
| Week 4 | Actual | 19 | 46.08 | 30.91 | | 20 | 45.40 | 25.18 | |
| | Change from Baseline | 18 | −8.58 | 40.92 | 0.4683 | 18 | −0.72 | 25.85 | 1.0000 |
| Week 6 | Actual | 19 | 42.57 | 30.84 | | 20 | 44.03 | 22.55 | |
| | Change from Baseline | 18 | −12.57 | 41.82 | 0.3038 | 18 | −1.32 | 27.27 | 0.9661 |
| Week 8 | Actual | 19 | 39.81 | 31.58 | | 20 | 43.93 | 23.18 | |
| | Change from Baseline | 18 | −16.41 | 41.95 | 0.1540 | 18 | −2.28 | 23.83 | 1.0000 |
| Week 10 | Actual | 14 | 37.44 | 32.33 | | 14 | 43.30 | 29.42 | |
| | Change from Baseline | 13 | −8.12 | 41.56 | 0.5417 | 12 | 4.87 | 34.38 | 0.9097 |
| | Change from End of Treatment | 14 | 1.44 | 9.71 | 0.7148 | 14 | 2.22 | 19.17 | 0.6698 |

For the Overall Symptom Score, there were larger improvements following treatment for Buspirone versus Placebo. For the Overall Severity Score, the mean score at baseline was 6.03 for Buspirone versus 6.24 for Placebo (Table 3). At the end of treatment, the mean score was 3.76 for Buspirone, while the mean score was 4.74 for Placebo. The mean change from baseline to end of treatment was significant for Buspirone (2.26 improvement, p=0.0005) and for Placebo (1.50 improvement, p=0.0076).

TABLE 3

Buspirone Capsules and Placebo in the Treatment Of Atopic Dermatitis
Summary of Overall Severity Score

| | | \multicolumn{7}{c}{Treatment} | | | | | | | |
|---|---|---|---|---|---|---|---|---|---|
| | | \multicolumn{4}{c}{Buspirone} | \multicolumn{4}{c}{Placebo} | | | | | |
| | | # | Mean | Std | p-value* | # | Mean | Std | p = value* |
| Baseline | Actual | 19 | 6.03 | 0.87 | | 21 | 6.24 | 0.83 | |
| Week 1 | Actual | 19 | 4.97 | 1.41 | | 21 | 5.12 | 1.61 | |
| | Change from Baseline | 19 | −1.05 | 1.42 | 0.0066 | 21 | −1.12 | 1.59 | 0.0065 |
| Week 2 | Actual | 18 | 4.89 | 1.51 | | 20 | 4.83 | 1.66 | |
| | Change from Baseline | 18 | −1.25 | 1.35 | 0.0017 | 20 | −1.45 | 1.34 | 0.0002 |
| Week 4 | Actual | 15 | 4.07 | 1.91 | | 17 | 5.03 | 1.43 | |
| | Change from Baseline | 15 | −2.03 | 1.80 | 0.0016 | 17 | −1.15 | 1.42 | 0.0067 |
| Week 6 | Actual | 14 | 3.29 | 1.97 | | 15 | 4.13 | 1.86 | |
| | Change from Baseline | 14 | −2.79 | 1.97 | 0.0010 | 15 | −2.00 | 1.68 | 0.0005 |
| Week 8 | Actual | 13 | 3.19 | 2.13 | | 16 | 4.06 | 2.06 | |
| | Change from Baseline | 13 | −2.85 | 2.15 | 0.0020 | 16 | −2.13 | 2.00 | 0.0008 |
| End of Treatment | Actual | 19 | 3.76 | 2.10 | | 21 | 4.74 | 2.29 | |
| | Change from Baseline | 19 | −2.26 | 2.16 | 0.0006 | 21 | −1.50 | 2.25 | 0.0076 |
| Week 10 | Actual | 14 | 3.04 | 2.34 | | 15 | 4.00 | 2.60 | |
| | Change from Baseline | 14 | −3.04 | 2.30 | 0.0007 | 15 | −2.13 | 2.52 | 0.0094 |
| | Change from End Of Treatment | 14 | −0.18 | 1.05 | 0.1404 | 15 | 0.03 | 0.85 | 0.9180 |

As shown in FIG. 13, there was a widening advantage for buspirone versus placebo. The initial buspirone disadvantage at baseline evolved into an advantage at the end of treatment (Week 8).

The results of all of the summary endpoints at the end of treatment, indicated that the patients treated with buspirone achieved significant improvements, compared to those treated with a placebo, as shown below in Table 4.

TABLE 4

| Endpoint | Buspirone | Placebo |
|---|---|---|
| Overall Score | 2.26 improvement | 1.50 improvement |
| Erythema | 0.89 improvement | 0.45 improvement |
| Induration | 0.61 improvement | 0.45 improvement |
| Pruritus | 0.76 improvement | 0.60 improvement |
| Lichenification | 0.47 improvement | 0.40 improvement |
| Vesiculation | 0.32 improvement | 0.17 improvement |
| Crusting | 0.53 improvement | 0.33 improvement |
| Oozing | 0.37 improvement | 0.07 improvement |
| Scaling | 0.71 improvement | 0.45 improvement |
| MD Global Response | 47% good-excellent | 33% good-excellent |
| PT Global Response | 42% good-excellent | 38% good-excellent |
| Pruritus VAS | 16 mm improvement | 2 mm improvement |

As shown in FIG. 13, patients with a overall baseline severity of 6 were seen to progress to a severity of approximately 3 over the course of a 10 week treatment.

Modifications and variations of the present invention relating to methods for treating atopic dermatitis, pruritis, hayfever, asthma and rheumatoid arthritis by topically or systemically administering an effective amount of buspirone or a buspirone derivative, or pharmaceutically acceptable salt thereof, will be obvious to those skilled in the art from the foregoing detailed description of the invention. Such modifications and variations are intended to come within the scope of the appended claims.

We claim:
1. A method for treating atopic dermatitis, hayfever, asthma, or pruritis in a human or other mammal that includes administering an effective amount of buspirone or its pharmaceutically acceptable salt.

2. The method of claim 1, wherein the condition to be treated is atopic dermatitis.

3. The method of claim 1, wherein the condition to be treated is asthma.

4. The method of claim 1, wherein the condition to be treated is hayfever.

5. The method of claim 1, wherein the condition to be treated is the ocular manifestation of atopic dermatitis.

6. The method of claim 1, wherein the condition to be treated is pruritis in a human.

7. The method of claim 1, wherein buspirone or its pharmaceutically acceptable salt is administered systemically.

8. The method of claim 7, wherein the method of systemic administration is oral.

9. The method of claim 7, wherein the method of systemic administration is intramuscular.

10. The method of claim 7, wherein the method of systemic administration is intravenous.

11. The method of claim 7, wherein the method of systemic administration is intraperitoneal.

12. The method of claim 7, wherein the systemic dosages is between 0.05 and 25 mg/kg.

13. The method of claim 7, wherein the systemic dosages is between 0.1 and 2.5 mg/kg.

14. The method of claim 7, wherein the buspirone or its pharmaceutically acceptable salt is administered in a pharmaceutically-acceptable diluent or carrier for systemic application.

15. The method of claim 1, wherein buspirone or its pharmaceutically acceptable salt is administered topically.

16. The method of claim 13, wherein buspirone or its pharmaceutically acceptable salt is administered in a pharmaceutically-acceptable diluent or carrier for topical application.

17. The method of claim 16, wherein the carrier is a mouthwash.

18. The method of claim 16 wherein the carrier is an inhaled aerosol.

19. The method of claim 16, wherein the carrier is an inhaled spray.

20. The method of claim 16, wherein the carrier is an intranasal aerosol.

21. The method of claim 16, wherein the carrier is an intranasal spray.

22. The method of claim 16, wherein the carrier is an ophthalmic carrier, and the compound and the carrier is topically applied to the eye.

23. The method of claim 15, wherein the topical administration comprises the inhalational treatment of hay fever.

24. The method of claim 15, wherein the topical administration comprises the inhalational treatment of asthma.

25. The method of claim 15, wherein the compound is applied cutaneously.

26. The method of claim 15, wherein the compound is applied to mucosal membranes.

27. The method of claim 15, wherein the daily dose of compound is between 0.01 and 60 grams.

28. The method of claim 15, wherein the compound is applied in a concentration between 0.01% and 10%.

29. The method of claim 15, wherein the compound is administered in a time release formulation.

30. The method of claim 15, wherein the compound is administered via a retention enema.

31. The method of claim 1, wherein the compound is administered in combination with another compound or compounds selected from the group consisting of antivirals, antifungals, antibiotics, anti-inflammatories, and other immunosuppressants and bronchodilators or other therapeutic agents for asthma.

32. The method of claim 1 wherein the mammal is a human.

* * * * *